United States Patent [19]

Vaccarello-Dunkel et al.

[11] Patent Number: 5,591,435

[45] Date of Patent: Jan. 7, 1997

[54] INSECTICIDAL OR INSECT BEHAVIORALLY ACTIVE PREPARATIONS FROM AROMATIC PLANTS

[75] Inventors: Florence Vaccarello-Dunkel, Bozeman, Mont.; David K. Weaver, Nova Scotia, Canada; Theodore W. Weaver, III, Bozeman, Mont.

[73] Assignee: The Research and Development Institute, Inc., Bozeman, Mont.

[21] Appl. No.: 231,934

[22] Filed: Apr. 25, 1994

Related U.S. Application Data

[63] Continuation-in-part of Ser. No. 801,817, Dec. 6, 1991, Pat. No. 5,306,497.

[51] Int. Cl.$^6$ .................................................... A01N 65/00
[52] U.S. Cl. ................. 424/195.1; 424/DIG. 10; 514/724; 514/725; 514/731; 514/736; 514/764; 514/919
[58] Field of Search ............... 424/195.1, DIG. 10; 514/919, 736, 724, 725, 731, 764

[56] References Cited

PUBLICATIONS

The Merck Index, 9th Ed. 1976 pp. 969, 962, 238, 239, 718, 362, 842, 821, 877, 1181, 123, 124, 1213–1215, 219.
N. McIndoo, Plants of Possible Insecticidal Value, USDA, 1945, pp. 34–36, 55, 106, 135, 136 & 140.
H. Lewis, Med. Botany, 1977, Wiley & Sons, New York p. 290.
Weaver et al., J. Stored Prod. Res., vol. 27, No. 4 "The Efficacy of Linalool, A Major Component of Freshly–Milled Ocimum Canum Sims (Lamiaceae), For Protection Against Postharvest Damage by Certain Stored Product Coleoptera", pp. 213–220, 1991.
Lambert et al., Insect Science Applications, vol. 6, No. 2, "Bruchid Control With Traditionally Used Insecticidal Plants *Hyptis Spicigera* and *Cassia Nigricans*", pp. 167–170, 1985.
Su, Journal of Economic Entomology, vol. 70, No. 1, "Insecticidal Properties of Black Pepper to Rice Weevils1 and Cowpea Weevils2,3,4", pp. 18–21, 1977.

*Primary Examiner*—John W. Rollins
*Attorney, Agent, or Firm*—Lowe, Price, LeBlanc & Becker

[57] ABSTRACT

Preparations from aromatic plants that are insecticidal or are insect behaviorally active, are used to control the development of insect populations. Leaves are milled or out drying to a small average particle size. Extracts and vapors may also be used. The resultant preparation, when contacted dry commodities or structures such as books or carpets, grain bins feed/flour mills, equipment, greenhouse or ornamental plants infested storage insects or insect infested perishable produce after harvest will reduce the insect population. In addition, soil may be fumigated the extracts.

24 Claims, 17 Drawing Sheets

INSECTICIDAL OR INSECT BEHAVIORALLY ACTIVE PREPARATIONS FROM AROMATIC PLANTS

This application is a continuation-in-part of application Ser. No. 07/801,817, filed Dec. 6, 1991, now U.S. Pat. No. 5,306,487.

FIELD OF THE INVENTION

The present invention involves a new approach to obtain and manufacture natural insecticidal or insect behaviorally active materials from aromatic plants. Note particularly, the invention provides a new approach to control insects from renewable non-petroleum sources.

BACKGROUND OF THE INVENTION

Many procedures are known in the prior art and commercially for insect control. The procedures commonly relied on or involve treatment of the insect with a toxic substance such as a synthetic chemical including the use of petroleum-based chemicals as the active ingredient or as the inert carrier material. These chemicals raise substantial environmental and health problems. The art continues to search for products and processes which will enable human to effectively control insects or modify their behavior. The present invention meets this need.

DISCLOSURE OF THE INVENTION

It is accordingly an object of the present invention to provide plant-based insect control preparations for insect management and control.

A further object of the present invention is to provide a method for the preparation of substances from aromatic plants which are useful to control unwanted or noxious insects or modify their behavior.

A still further object of the present invention is to provide insecticidal compositions which are produced from natural plants and which are effective to manage or control insects or modify their behavior.

A further object is to provide the chemical extracts of insecticidal compositions which are produced from natural plants and which are effective to manage or control insects or modify their behavior. The term chemical as used herein included extracts of processed plant materials, components of the chemical extracts or synthetic chemicals which duplicate extract components.

Other objects and advantages of the present invention will become obvious as the description thereof proceeds.

In satisfation of the foregoing objects and advantages, the present invention provides an insecticidal composition prepared from aromatic plants which are lethal to insects or are effective to control insect behavior by controlling the development of insect populations or their movement. The composition is dispersed into an area fostering insects and may be used as a repellent.

The compositions of the invention are prepared from plants which are harvested after leaf maturation, and then milled to a small particle size. The resulting product is then combined with dry commodities or the volatiles of these compositions are released into these commodities and structures. The compositions can be administered to household furnishings, museum holdings, artifacts, insect collections, pieces of art, books, etc., infested with storage insects, insect-infested perishable produce after harvest, or used to fumigate the soil or structures (such as feed mills, flour mills, farm machinery such as harvesting machinery, empty grain bins, empty greenhouses). These compositions are new sources of natural materials for insect management which do not involve the use of petroleum-based chemicals.

BRIEF DESCRIPTION OF THE DRAWINGS

Reference is now made to the drawings accompanying this application, wherein

In FIG. 10, bars 1–3 represent controls exposed to lesser grain borers *Rhyzopertha dominica* (F); bars 4 and 5 represent *Artemesia tridentata* exposed to preparations in accordance with the invention.

DESCRIPTION OF PREFERRED EMBODIMENTS

Figure 1:
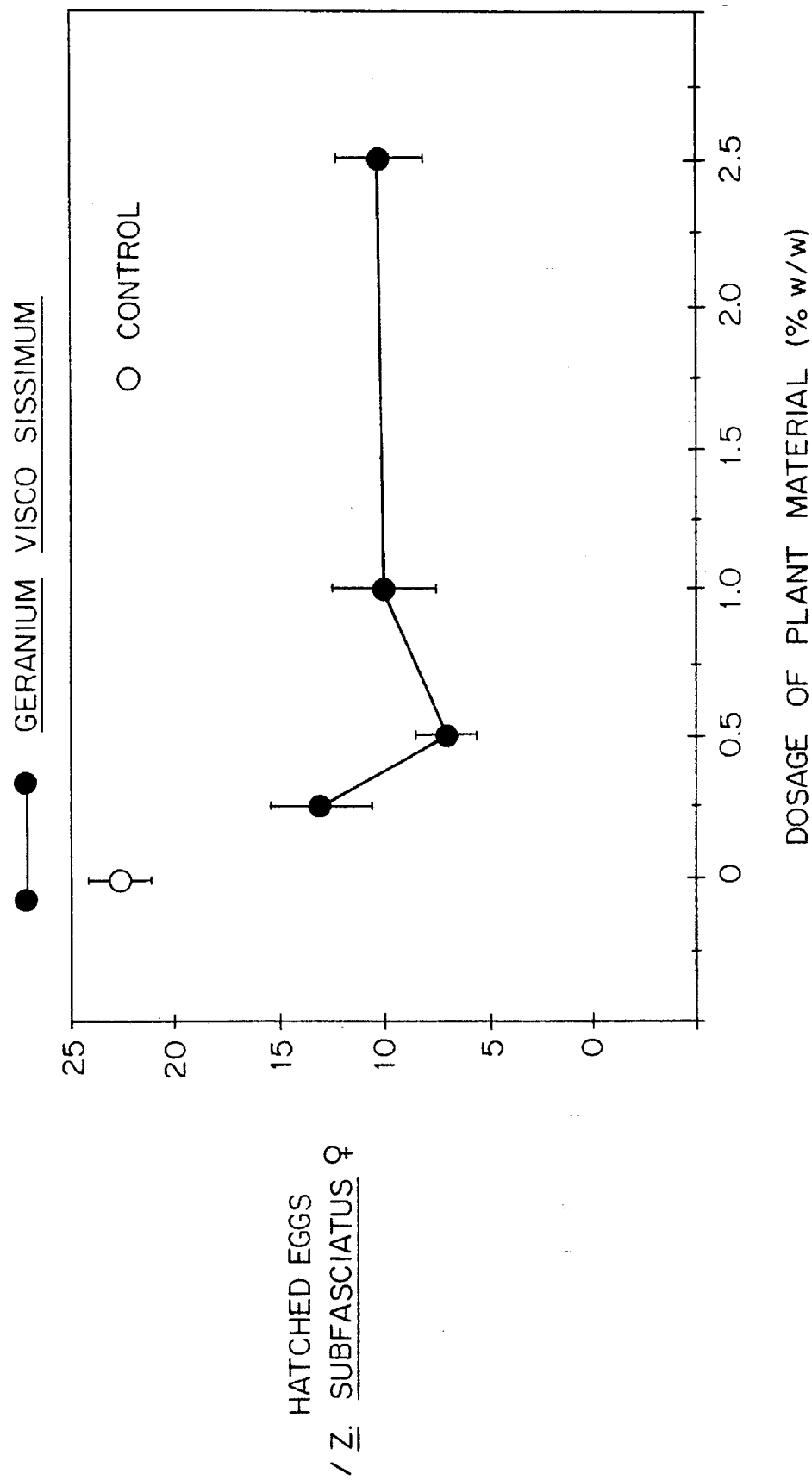
FIGS. 1, 2, 3, and 4 are graphs which demonstrate the effect on the number of hatched eggs of the insect *Z. subfasciatus* with respect to four different species of plants of this invention.
Figure 2:
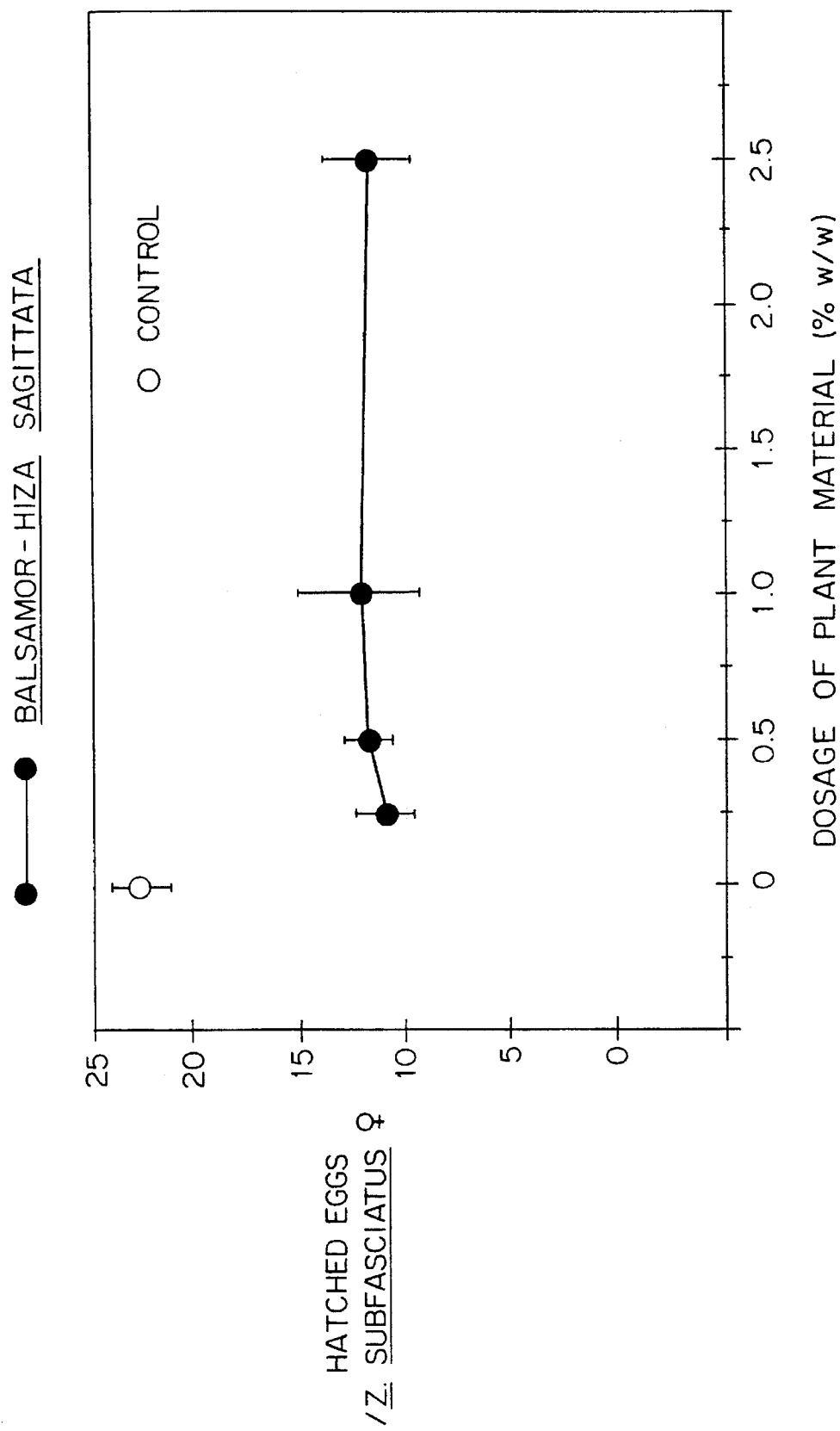
Figure 3:
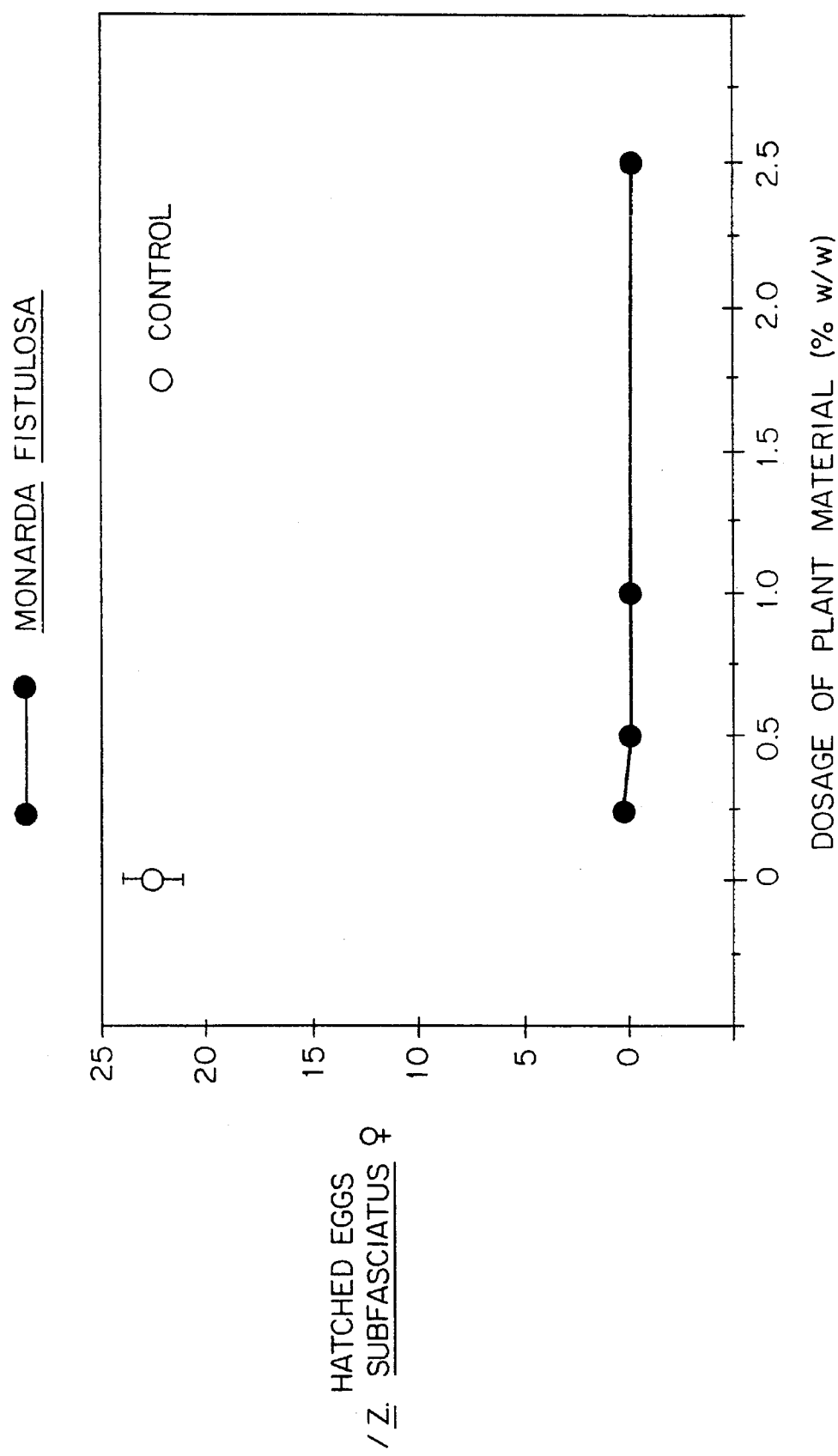
Figure 4:
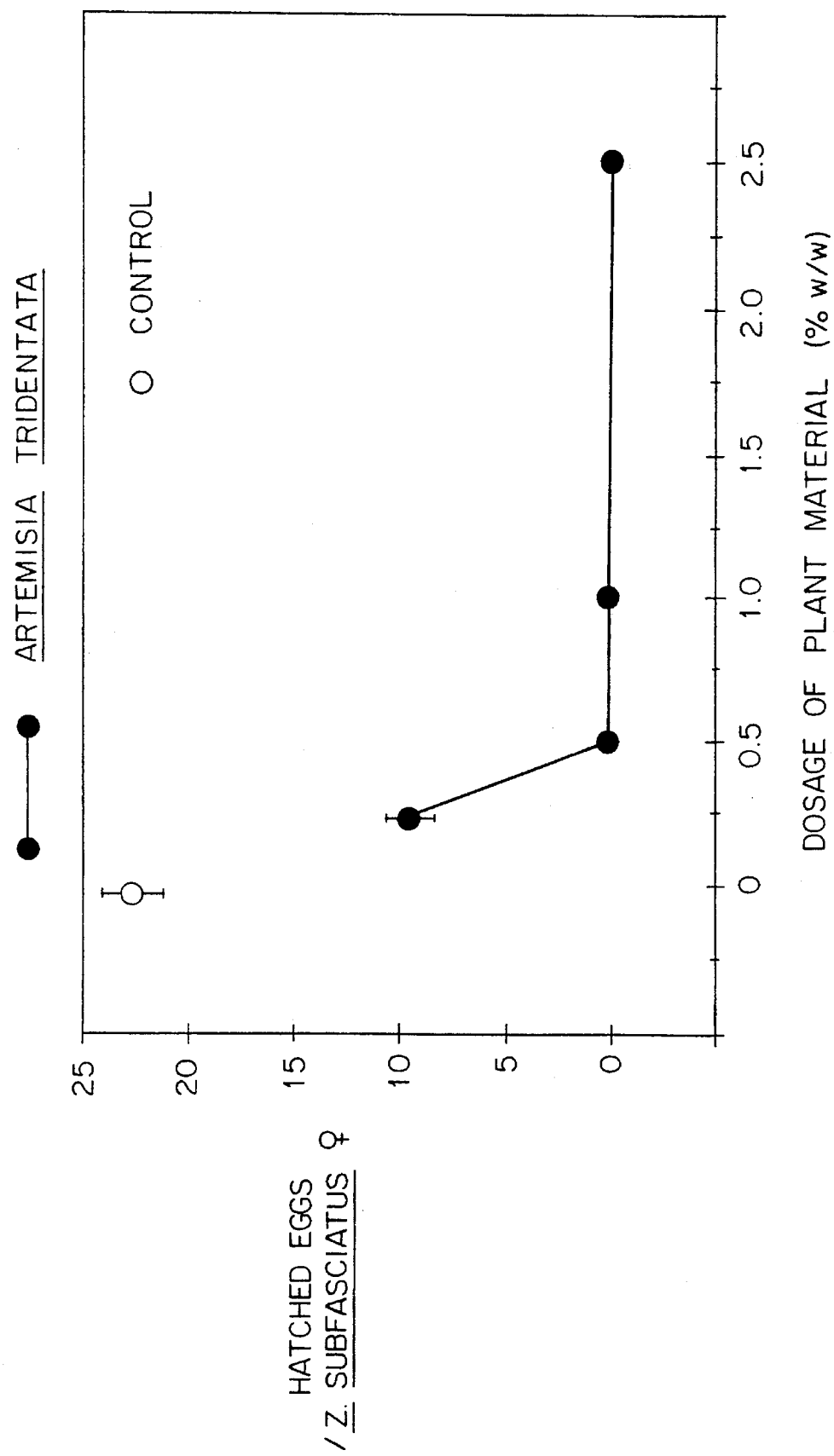

The present invention is concerned with a new approach to insect control and management and provides methods for reducing insect populations and/or control of insect behavior. The present invention represents a significant step in this art since it is not based on the use of petroleum-based chemicals, non-renewable resources or imported resources and therefore, does not present hazards to health and the environment. The invention is based on the recognition that certain plants which are aromatic in nature can be processed to provide an insect control composition or preparation.

The present invention is based on the use of aromatic plants which are insecticidal or insect behaviorally active and which can be processed to a form which will be effective to be lethal to insects or to control the development of insect populations. The invention is considered to be broadly applicable to any plant which has the necessary characteristics for insect management or control. Aromatic plants are particularly useful, with plants of the mint family or the genus Artemesia being preferred. In this invention, the compositions and methods are demonstrated by providing examples of five different aromatic plants defined herein below by common name and scientific name:

1. Sticky Geranium, *Geranium viscosissimum;*
2. Balsam Root, *Balsamorhiza sagittata;*
3. Sagebrush, *Artemesia tridentata;*
4. African Mint, *Ocimum canum;*
5. Bergamot's Mint or Horse Mint, *Monarda fistulosa*

While these five species have been found useful in the invention, it is considered that many other plants and especially aromatic plants are useful in accordance with the methods described in this invention. Therefore, these examples are not construed in any way to be limiting to the invention with respect to the plants disclosed.

The compositions of the present invention are particularly useful in insect control in closed environments such as in packing cases or for stored commodities, and for control of insects in greenhouses and the like. The compositions of the present invention are also useful in soil fumigation. In use, preparations of the composition or their volatiles are introduced into the packing cases or in contact with the stored commodities where insects are often a problem.

In soil fumigation, the composition is introduced into the soil or the soil is coated with the composition. The amount of composition used will vary with the insect infestation present or expected but should range from about 0.1 to 99 wt. %, preferably 0.25 to 10 wt. % of the material being protected. Since the composition of this invention is not toxic, nor a threat to the environment, the amount to be used is not critical.

In accordance with this invention, the insects will be destroyed or killed directly or the reproduction abilities of the insects will be reduced.

The composition of the invention is prepared by harvesting leaves from the desired plant or mixture of different species or varieties of species in a random pattern while including petioles but not stem material. The collection or harvest is then dried either in bulk or in containers in an oven or the like to remove moisture. Heating in an oven at 95° F. to 150° F. for 1 to 72 hours is usually sufficient. The dried plant material is then milled preferably to a final average particle size which is about 2.0 mm or smaller. It has been found as shown in the examples below that the smaller particle size increases the effectiveness of the composition.

In accordance with the invention, liquid extracts and vapors from the aromatic plants are also useful for insect control. For example, sagebrush vapors can be used effectively.

The resulting milled leaf tissue may then be added in a range of concentration as discussed above to the stored product to be protected or soil to be fumigated. Mixing may be done by hand or by machine in a conventional manner. Processed leaves and flowers, even 96 hours after processing (in a 72 hour test) retain insecticidal activity, however, insecticidal activity is slightly reduced from freshly processed plant material. Finely milled flowers are also efficacious insecticides, but are less active than finely milled leaves.

It has been discovered that the plant material prepared in accordance with this invention is extremely effective in reducing insect concentrations and preventing their proliferation without risks to health or the environment. The composition of the invention is useful in insect control against a wide variety of insects including those found in the storage of commodities such as beans, potatoes, tomatoes, bananas, papayas and other perishable tropical fruits grains such as barley, wheat and corn. The composition of the invention is effective against the bean bruchid, fruit flies, bastrichids, such as grain borers, dermestids and the like.

The following examples are presented to illustrate the invention, but it is not considered to be limited thereto. In the examples, parts are by weight unless otherwise indicated.

Figure 10:
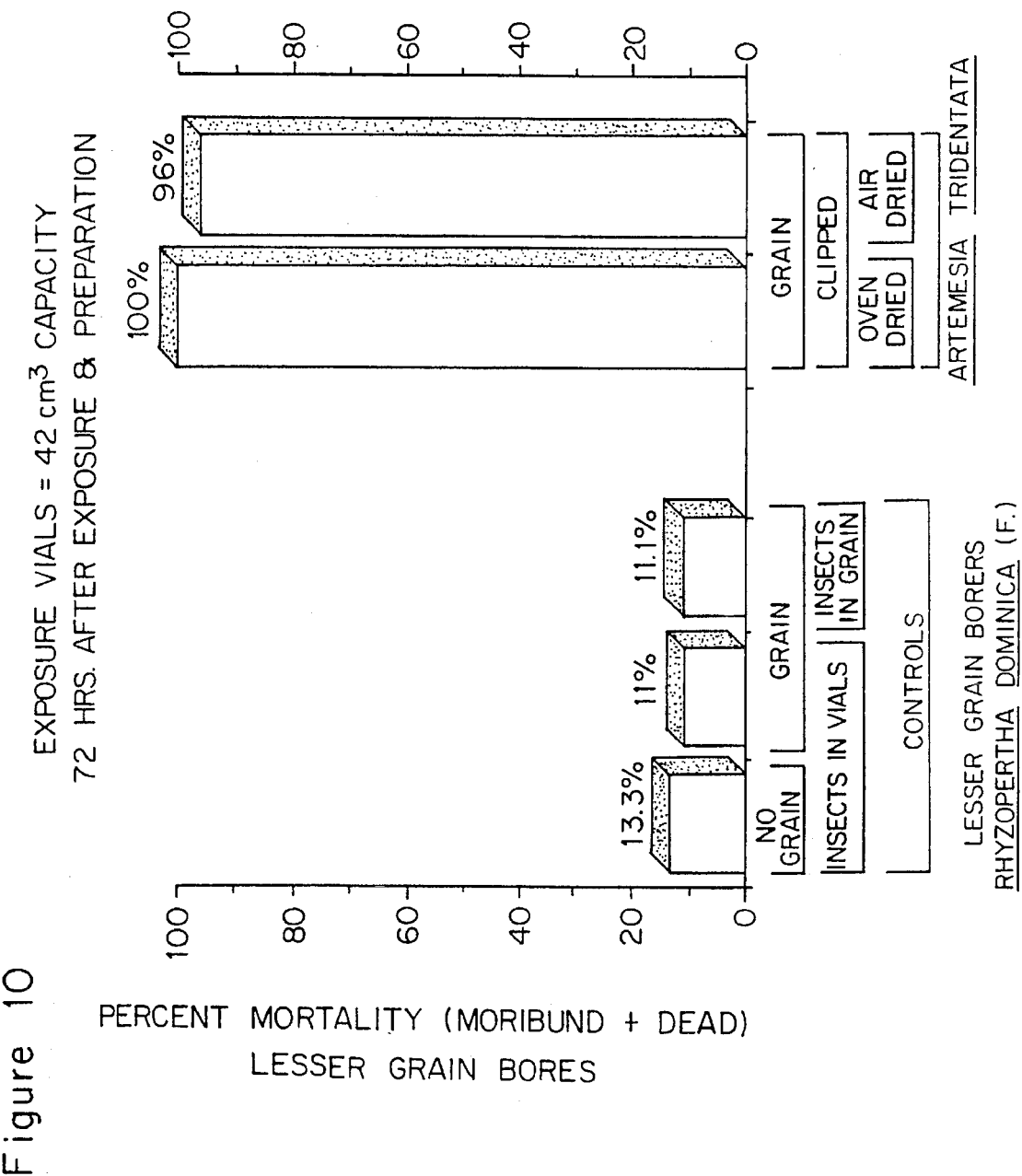
FIGS. 10 and 11 show the results of a 42 cm$^3$ grain bin study in which lesser grain borers were killed by *Artemisia tridentata* leaves processed in accordance with the present invention. The results were taken 72 hours after exposure and preparation.

Example 1: Plant material was prepared by harvesting leaves in a random pattern both as to individual plants and to location of leaf on each plant. The collection included petioles by not stem material which was removed prior to drying. Leaves were placed in paper bags in the plant drying room at 125° F. for 72 hours. Air drying for 96 hours is also sufficient preparation as shown in FIG. 10. The plant material was then removed, cooled, and milled in a blender for 1.5 minutes. The final particle size was less than or equal to 2.0 $mm^2$. The preference for the precision of this size is further illustrated in Example 4 and Example 7. The milled leaf tissue was then added immediately in a range of concentrations, each in ten replications, to plastic vials containing the stored product to be protected and mixed by rotation as described in the following examples. For purposes of some bioassays, but not in actual practice, the milled material was also tested directly without the stored commodity.

Example 2: The techniques in Example 1 were used with *Geranium viscosissimum, Balsamorhiza sagittata, Artemesia tridentata,* and *Monarda fistulosa* in dry pinto beans (*Phaseolus vulgaris*) to control the bean bruchid, *Zabrotes subfasciatus.* Ten replicates were made of four concentrations (weight of plant material/weight of dry beans) 0%, 0.25%, 0.5%, 1.0%, and 2.5%. Each vial was inoculated with five male and five female *Z. subfasciatus* 0–1 day after emergence from stock culture beans as adults. This experiment was maintained under the same conditions that test insects were reared in stock culture, 12:12::light:dark photoperiod, 65±5% Relative Humidity, and 27°±1° C. After 25 days, mean number of eggs laid per female were determined, and mean % of eggs hatched were determined.

Example 3: Using the techniques in Examples 1 and 2, the following results were obtained (refer to four attached graphs of FIGS. 1, 2, 3, and 4). The mean number of eggs laid by *Z. subfasciatus* were not significantly different from the mean number of eggs hatched per female for each of the plant preparations to which they were exposed. That is, regardless of the concentration, most of the eggs that were laid, subsequently hatched. Therefore, there is presented only the data for the eggs hatched per female. With *G. viscosissimum* and *B. sagittata* the hatched eggs per female was decreased by over half at concentrations of 0.5% or above in comparison to the control without any plant material. With *M. fistulosa,* there were no eggs hatched (and no eggs laid) at concentrations of 0.25% or above. With *A. tridentata,* there were no eggs hatched (or laid) at concentrations of 0.5% or above.

Figure 9:
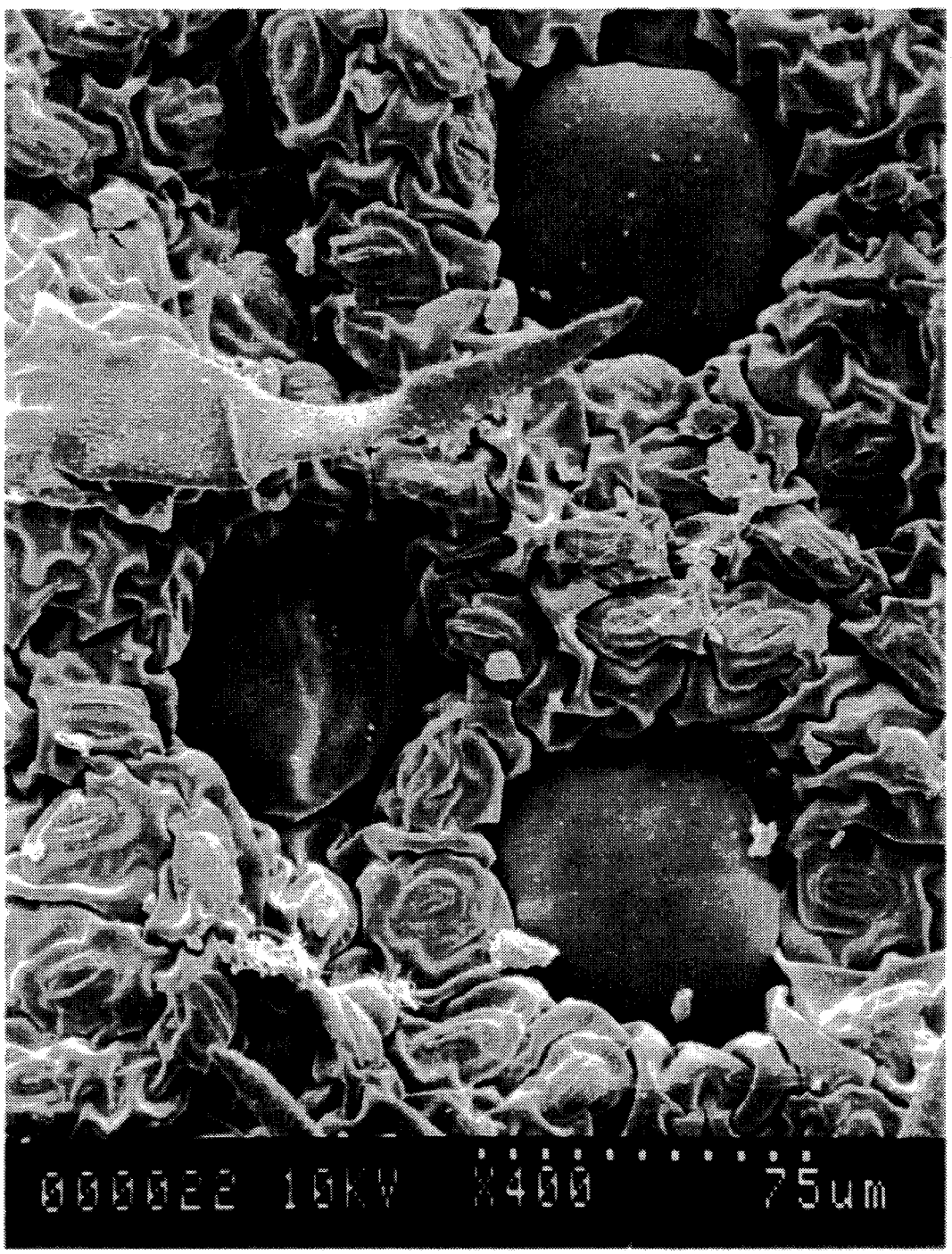
FIG. 9 shows a closeup of the glandular hair on intact leaf *Ocimum canum* leaf, storage unit for linalool and other components of the essential, insecticidal oil. The view are of the glandular hairs or trichomes which are sunken or closely adhering to the leaf surface and is typical of leaves that produce insecticidal fumigants when dried and finely milled.

Example 4: Trials were also run with *O. canum* whole vs. milled leaves with milled leaves that were larger than the claimed size which releases insecticidal compounds from the glandular hairs (trichomes) see FIG. 9. The bruchids *Acanthoscelides obtectus* and *Z. subfasciatus* were exposed to 1 g milled leaves mean size 2.0 to 5.0 $mm^2$ and to 1 g whole leaves of this mint plant. After 15 minutes, 84 of 100 adult *A. obtectus* were normal and 16 had difficulty walking. No abnormal response was obtained in the insects exposed to whole leaves or in similar chambers without any leaves. After 72 hours, 18 were dead in the coarsely milled replicates and 82 were normal. Similar results were obtained with *Z. subfasciatus*. With 1 g leaves of the same mint species milled to the size indicated in Example 1, 100% of the adult male *Z. subfasciatus* tested were dead after 24 hours and after 48 hours, 50% of the females were dead. There was no mortality in the controls.

Example 5: Fumigation tests were conducted with two of the Rocky Mountain plants. Material prepared as described in Example 1 was placed in three concentrations (0, 0.1 g and 1.0 g) with three replicates in 42.5 ml glass vials. Insects were placed individually in smaller vials that were suspended in the larger vial. The covering of the smaller vial allowed sufficient gas exchange. Moribundity in 24 hours was followed by death in 72 hours with milled leaves of *A. tridentata* for 100% of the adult *Z. subfasciatus* tested. FIGS. 1, 2, 3 & 4 are *Z. subfasciatus* results. There were no moribund or dead individuals in either the 0 g or the 0.1 g concentrations. With the same experimental design, leaves of *M. fistulosa* were tested and found to cause moribundity in 100% of the adult *Z. subfasciatus* tested. 33% of the individuals in the 0.1 g concentration were moribund at 72 hours and dead at 120 hours.

Figure 11:
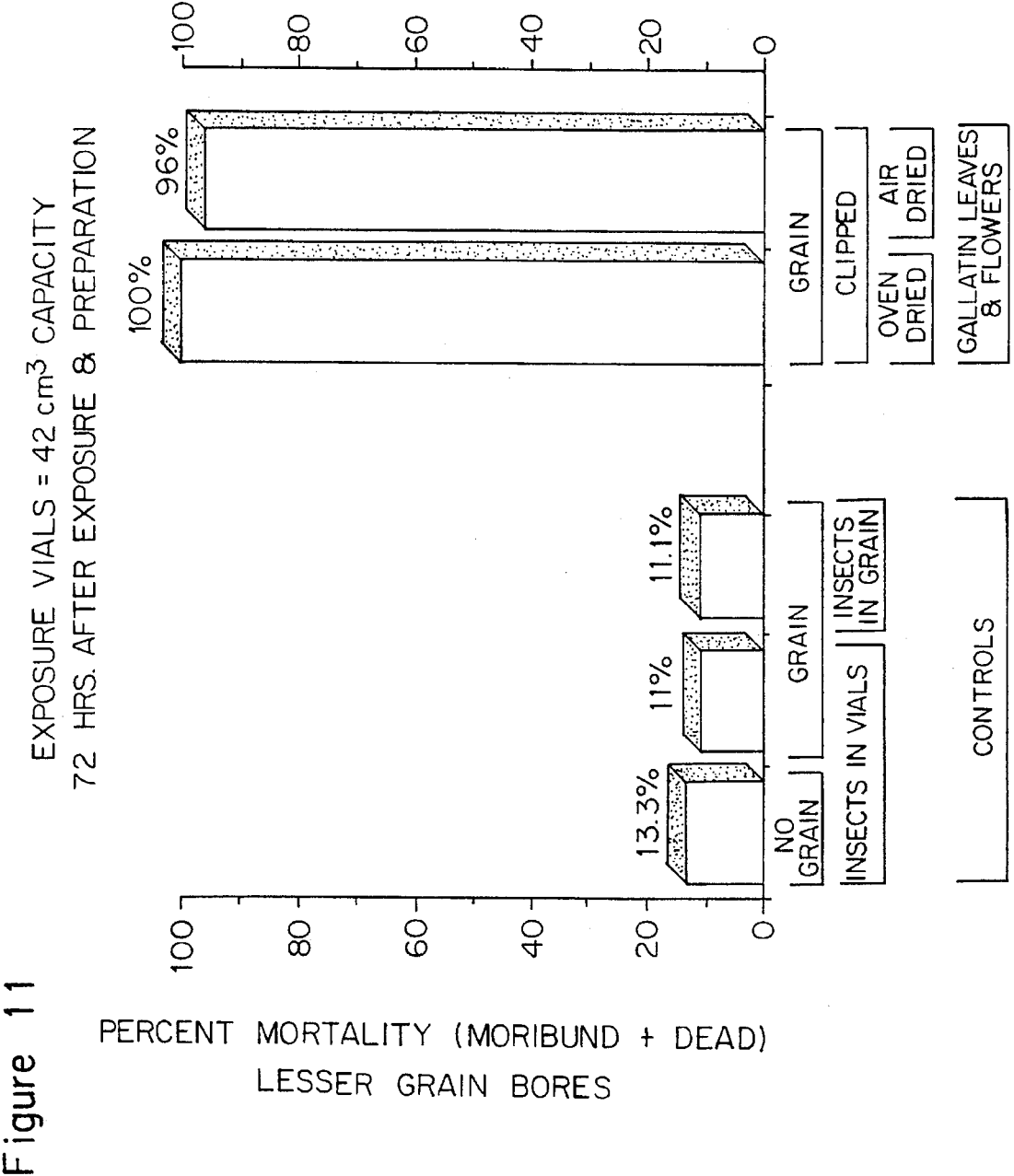
Figure 12A:
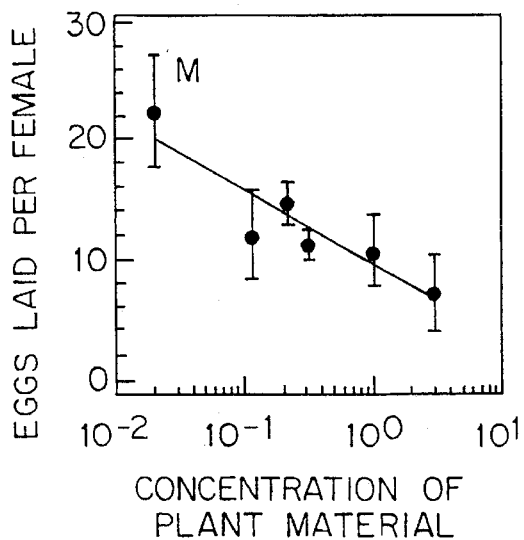
FIGS. 12(a)–12(d) shows the mean number of eggs laid per female (±S.E.) in 1 g of soft white wheat exposed to five male *S. oryzae* (4–9 days old, allowed to oviposit for 7 days after which they were removed and the immature cohorts were incubated for another 7 days prior to termination by freezing), as influenced by increasing concentration of plant material. Plant species and concentration units as indicated in FIG. 1. Regression equations: M–EGGS LAIDS PER FEMALE=a+b(ln CONCENTRATION), a=9.83, b=−2.64, lack-of-fit F=1.63, df=4, 30, P<0.05, r$^2$=0.44 percentage of maximum attainable r$^2$=82%; A–EGGS LAID PER FEMALE=a+b/CONCENTRATION, a=8.73, b=0.26, lack-of-fit F=0.94, df=4, 32, P>0.05, R$^2$=0.60, percentage of maximum attainable r$^2$=94%, B–EGGS LAID PER FEMALE=a+b/CONCENTRATION, a=14.57, b=0.16, lack-of-fit F=1.06, df=4, 31, P>0.05, R$^2$=0.25 percentage of maximum attainable r$^2$=74%, G–EGGS LAID PER FEMALE=a+b/CONCENTRATION, a=9.64, b=0.24, lackof-fit F=0.07, df=4, 28, P>0.05, $R^2$=0.52 percentage of maximum attainable $r^2$=79%.
Figure 12B:
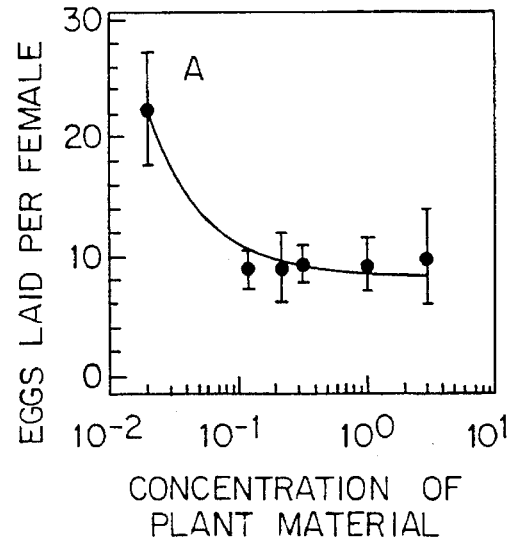
Figure 12C:
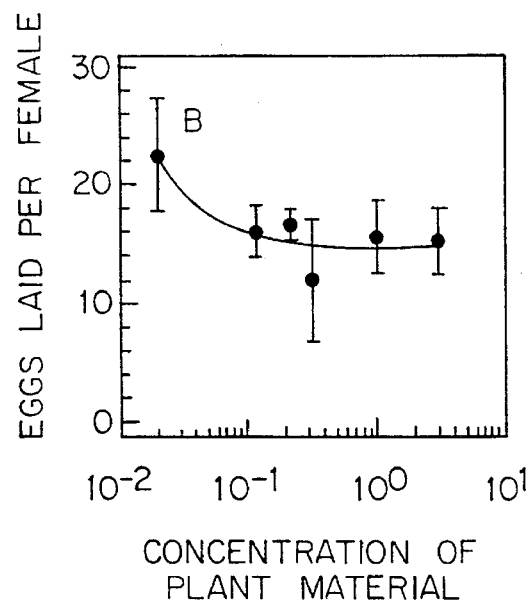
Figure 12D:
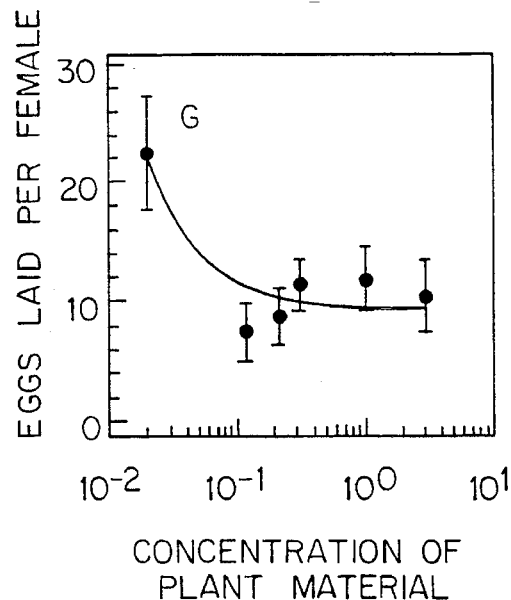
Figure 13A:
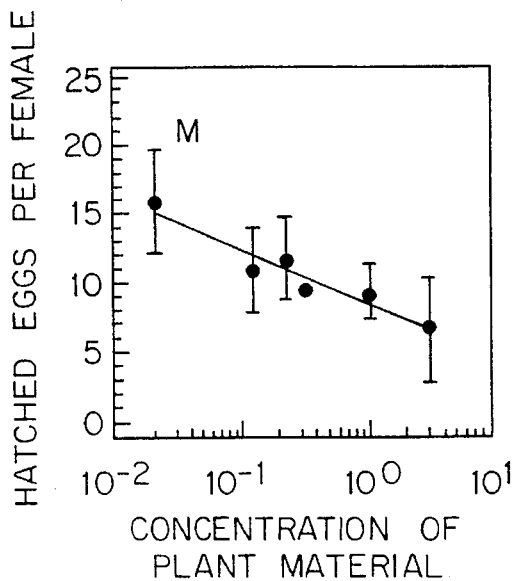
FIGS. 13(a)–13(d) shows the mean number of hatched eggs per female (±S.E.) in 1 g of soft white wheat exposed to five mal and five female S. oryzae (4–9 days old, allowed to oviposit for 7 days after which they were removed and the immature cohorts were incubated for another 7 days prior to termination by freezing), as influenced by increasing concentration of plant material. Plant species and concentration units as indicated in FIG. 1. Regression equations: M–HATCHED EGGS PER FEMALE=a+b(ln CONCENTRATION), a=8.78, b=1.63, lack-of-fit F=1.58, df=4, 32, P>0.05, $R^2$=0.49 percentage of maximum attainable $r^2$=85%; B–HATCHED EGGS PER FEMALE=a+b/CONCENTRATION, a=7.42, b=0.17, lack-of-fit F=1.58, df=4, 32, P>0.05, $R^2$=0.49 percentage of maximum attainable $r^2$=85%; B–HATCHED EGGS PER FEMALE=a+b/CONCENTRATION, a=12.34, b=0.067, lack-of-fit F=1.68, df=4, 31, P>0.05, $R^2$=0.09 percentage of maximum attainable $r^2$=36%; G–HATCHED EGGS PER FEMALE=a+b/CONCENTRATION, a=9.38, b=0.12, lack-of-fit F=2.54, df=4, 28, P>0.05, $R^2$=0.24 percentage of maximum attainable $r^2$=55%.
Figure 13B:
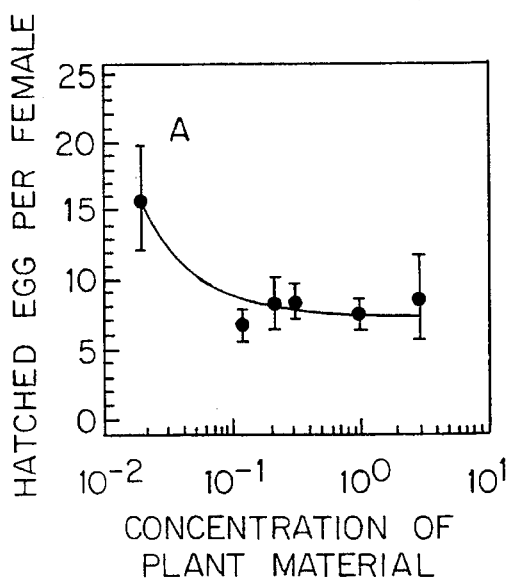
Figure 13C:
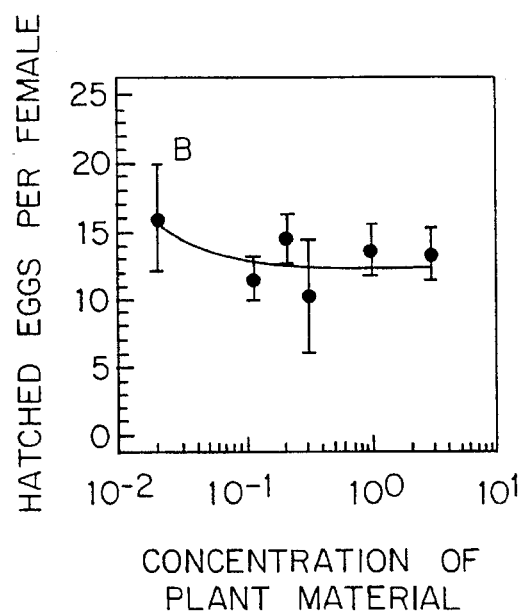
Figure 13D:
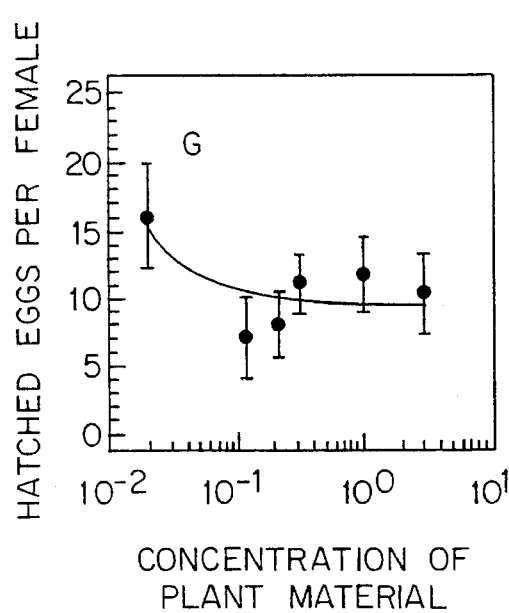

Also adult lesser grain borers, *Rhyzopertha dominica* were used in fumigation tests with *A tridentata* at 0.029 $g/m^3$ concentration. For this the LT50 was 9 hours. These results are shown in FIGS. 10 and 11 attached.

A larger mini-bin (960 $cm^3$) study was also conducted which provided similar results to the 42 ml above.

Example 6: Fumigation tests were also run with linalool, a known insecticidal component of leaves of *O. canum*, in similar small vials suspended within 42.5 ml glass vials, as used in Example 5. Similar results were obtained. The concentration of linalool released from 1 g of milled *O. canum* resulted in an LT50 of 15 hours for female *Z. subfasciatus*.

Example 7: Vapors released from sagebrush, *A. tridentata,* reduced the development of fruit flies, *Drosophila melanogaster,* from eggs and reduced the fitness of resultant animals. The fruit flies resided in 200 ml bottles capped with cotton and partially filled (1 cm) with standard cornmeal-yeast medium. Fly development was compared in bottles containing a gauze bag containing nothing, whole sagebrush leaves (2 or 5 g samples), or crushed sagebrush leaves (prepared with a mortar and pestle to a particle size less than or equal to 1 mm2) (2 or 5 g samples). Three observations were made:

1) The percentage of eggs yielding adult flies declined with exposure to aromatic substances, while 76% of no-treatment animals reached adulthood and a similar 70–74% of individuals exposed to uncrushed leaves (2 g and 5 g) yielded adults, 10% fewer individuals survived exposure to crushed sagebrush (66 and 64% for 2 g and 5 g treatments, respectively).

2) Sage vapors had a lasting effect such that females exposed to sage vapors were less fit (i.e., saw fewer offspring to adulthood) than untreated females; females raised in sage vapors produced, in the absence of sage vapors, 43–60% (with 2 and 5 g samples) as many offspring as females raised in their absence.

3) The effect was aggravated, however, if the offspring were also raised in the presence of sage vapors; females raised in the presence of sage vapors raised 10–20% as many offspring in sage vapors as females raised in their absence.

Example 8: Extraction and Analysis of Plant Extracts

Five grams of the processed material from each plant were extracted separately in 50 ml of 1:4 isopropanol: hexane (both HPLC grade) and 1.3 mg of n-decane was added as an internal standard. The crude extracts were subjected to flash column chromatography on a 1.9 cm diameter×10 cm column packed with TLC grand MgO. Samples were then concentrated under cool $N_2$ to approximately 3 ml. The concentrated samples were then subjected to a second flash chromatography procedure on a 1.0 cm diameter×11.5 cm column. Samples were then evaporated under cool $N_2$ to near dryness and then resolvated in 1.5 ml of HPLC grade hexane.

Extracts were subjected to gas chromatographic (GC) analyses on two separate instruments. Initial inspection of the extracts and ultimate quantification of volatiles were done on a Hewlett Packard 5190 GC equipped with a flame ionization detector (FID). The column used was a 30 m×0.252 mm i.d. DB-1 (J and W Scientific, Folsom, Calif.) with a He flow of 1 cm/sec. The injector was set at 225° C., the detector at 280° C., and the column oven programmed at 60° C. for 30 sec., then increased to 270° C. at 10° C./min., and held at 270° C. for 20 min. The injector purge was operated in split mode throughout. Output went to a Hewlett Packard 3392A integrator recorder and quantities of detected compounds were calculated by comparison of the area under the decane peak with press under sample peaks.

GC-mass spectrometric (GC-MS) analyses were made using a Shimadzu GC-14A coupled to a Finnigan Model 800 series Ion Trap Detector. The injector oven was set at 230°

C. and the heated transfer line to the MS was set at 265° C. The column was also a 30 m×0.252 mm DB-1, temperature-programmed at 40° C. for 30 sec., then 20° C./min to 60° C., held for 1 min., then increased to 280° C. at 10° C./min., and held at 280° C. for 20 min. Injection was made with the splitter closed initially, but then opened at 30 sec. The MS was operated in the full scan mode, ranging from 35 to 350 amu at one scan per sec.

Tentative identifications were made by matching background-subtracted sample spectra with those in the National Bureau of Standards mass spectral library and with those in the terpene library of Adams (1991) using the Finnigan ITDS software. Confirmation of library matches were made by matching retention time and spectra of authentic samples.

Results: Total ion current chromatograms of plant extracts are given in FIG. 5 and identifications and quantities of compounds are given in Table 1.

*A. tridentata* contains the largest number of extractable volatiles, primarily terpenoids with camphor and cineole being most abundant (FIG. 5 and Table 1).

*M. fistulosa* also contains a significant number of volatile compounds, with carvacrol being most abundant (FIG. 5 and Table 1). Amount of carvacrol extracted from *M. fistulosa* was nearly three time greater than that for the next most abundant compound extracted, camphor from *A. tridentata*.

Both *B. sagittata* and *G. viscosissimum* contain limited quantities of volatile material, with germacrene from *B. sagittata* being the only identified compound present in greater than 1 mg/g quantities (FIG. 5 and Table 1).

Example 9: The following are the identities and quantities of volatiles extracted from four species of Rocky Mountain plants. The extracts possess natural insecticidal or insect behaviorally active properties. The term extracts used throughout the specification and claims includes synthetic compounds corresponding to the compounds found in natural extracts.

TABLE 1

| Species | Peak No.[1] | Retention Time (sec)[1] | Compound Name | Evidence | Quantity (mg/g)[3] or % of extract |
|---|---|---|---|---|---|
| *Artemisia tridentata* | 1 | 325 | alpha-Pinene | C | 0.264 1.25% |
| | 2 | 338 | Camphene | C | 0.821 3.8% |
| | 4 | 361 | Sabinene | L | 0.139 0.64% |
| | 7 | 418 | 1, 8-Cineole | C | 4.004 18% |
| | 9 | 441 | Artemisole | L | 0.495 2.3% |
| | 11 | 452 | cis-p-menth-2-en-1-ol | L | 0.704 3.3% |
| | 13 | 488 | alpha-Thujone | C | 0.629 3.0% |
| | 14 | 501 | Myrtenal | L | 0.562 2.6% |
| | 15 | 531 | Camphor | C | 9.708 45% |
| | 16 | 542 | Pinocarvone | L | 0.069 0.32% |
| | 17 | 554 | Borneol | C | 0.844 3.9% |
| | 18 | 564 | cis-Sabinene hydrate | L | 0.047 0.21% |
| | 19 | 576 | alpha-Terpineol | C | 0.567 2.5% |
| | 20 | 614 | Undet.Oxyg. Terpenoid | S | 0.154 0.7% |
| | 23 | 667 | Isobornyl | L | 0.224 |

TABLE 1-continued

| Species | Peak No.[1] | Retention Time (sec)[1] | Compound Name | Evidence | Quantity (mg/g)[3] or % of extract |
|---|---|---|---|---|---|
| | | | acetate | | 1.0% |
| | 25 | 732 | Geranyl formate | L | 0.234 1.1% |
| | 26 | 753 | Ocimenone | L | 0.185 0.85% |
| | 27 | 799 | trans-Caryophyllene | C | 0.338 1.5% |
| | 28 | 849 | Germacrene | L | 0.707 3.3% |
| | 30 | 902 | Nerolidol | L | 0.069 0.32% |
| | 31 | 914 | Undet. sesquiterpene | S | 0.218 1.0% |
| | 32 | 993 | Undet. sesquiterpene | S | 0.355 1.6% |
| | 33 | 1021 | Undet. sesquiterpene | S | 0.208 1.0% |
| *Balsamorhiza sagittata* | 27 | 799 | trans-Caryophyllene | C | 0.492 14% |
| | 28 | 849 | Germacrene | L | 2.149 61% |
| | 29 | 860 | Bicyclogermacrene | L | 0.457 13% |
| | 35 | 1275 | Phytol | C | 0.405 11% |
| *Geranium viscosissimum* | 34 | 1108 | Undet. C19 hydrocarbon | S | 0.150 33% |
| | 35 | 1275 | Phytol | C | 0.303 67% |
| *Monarda fistulosa* | 3 | 359 | 1-Octen-3-ol | C | 0.250 0.7% |
| | 5 | 379 | Myrcene | C | 0.219 0.6% |
| | 6 | 411 | para-Cymene | C | 2.079 5.6% |
| | 8 | 419 | Limonene | C | 0.136 0.36% |
| | 10 | 449 | gama-Terpinene | C | 1.329 3.6% |
| | 12 | 485 | Linalool | C | 0.132 .36% |
| | 21 | 624 | Thymoquinone | C | 0.569 1.5% |
| | 22 | 666 | Thymol | C | 3.412 9.2% |
| | 24 | 684 | Carvacrol | C | 26.285 71% |
| | 28 | 847 | Germacrene | L | 0.419 1.1% |

Figure 5A:
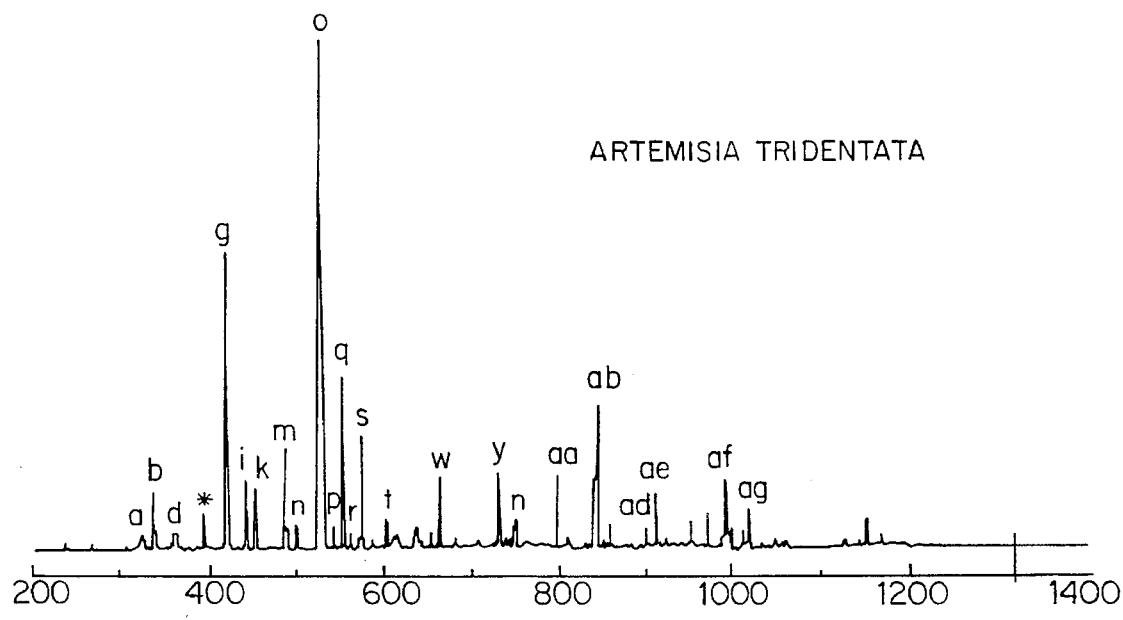
FIGS. 5(a)–5(d) shows the total ion current chromatograms of volatiles extracted from four species of plants obtained on a DE-1 column. Retention times are given in seconds on the x-axes, IS-internal standard of n-decane added to each sample at 1.33 mg; identities and quantities of numbered peaks are given in Table 1.
Figure 5B:
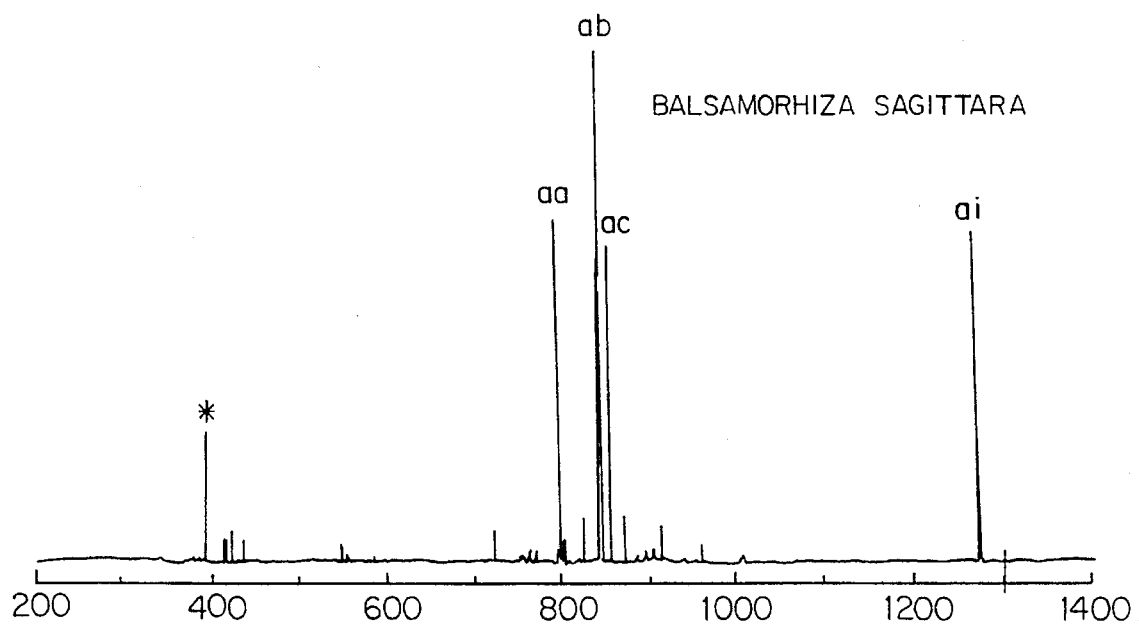
Figure 5C:
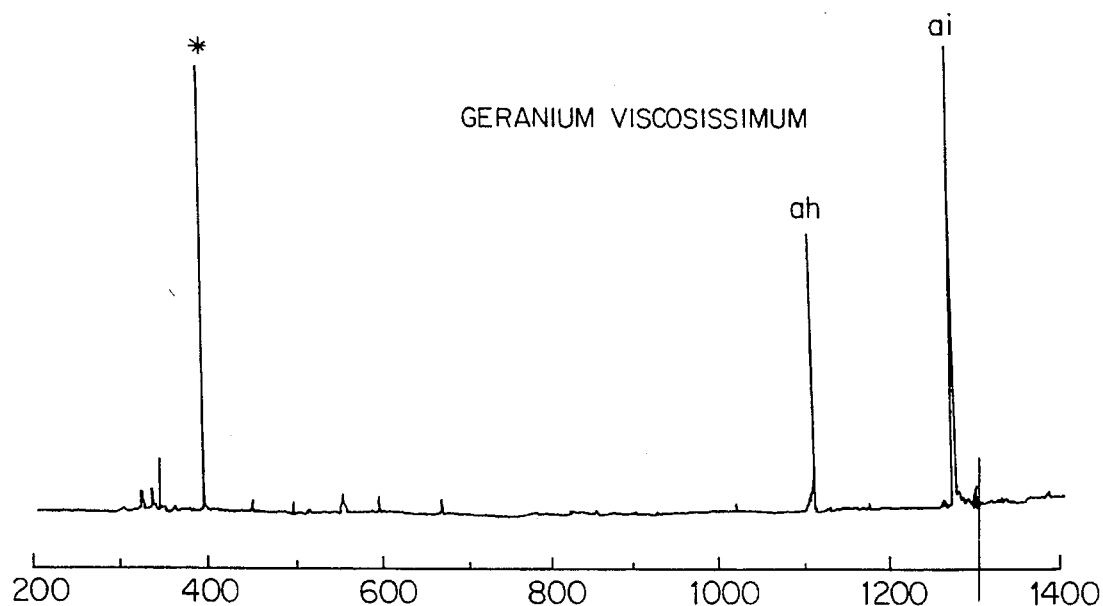
Figure 5D:
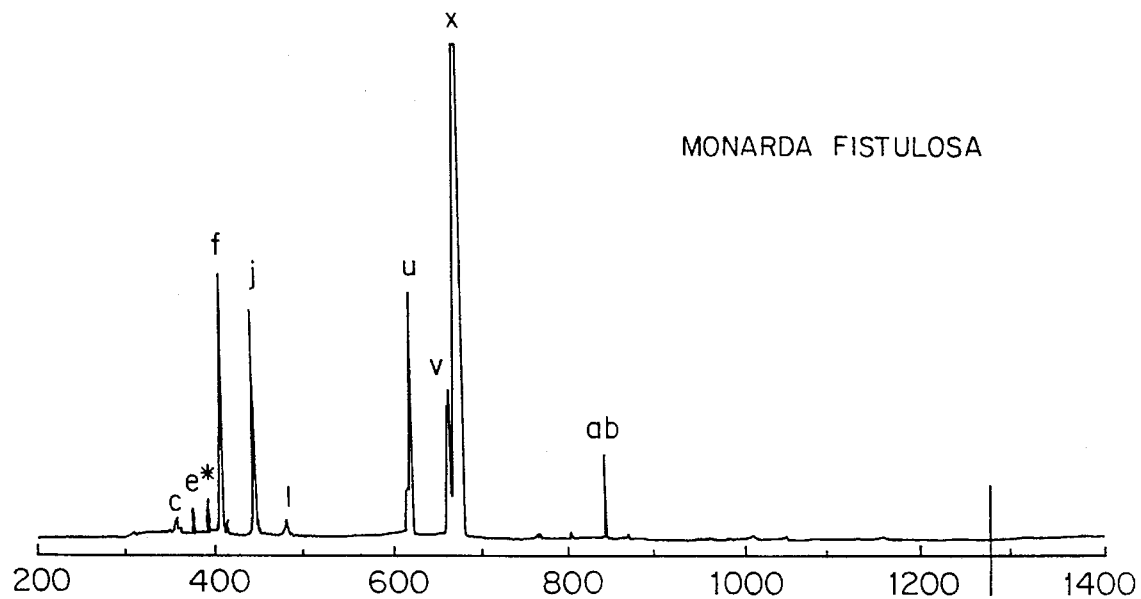

[1]Peak numbers and retention times correspond to those in FIG. 5Identity of peaks determined to following ways: C-confirmed by comparison with retention time and spectrum of authentic material; L-identity assigned based on match of sample spectrum to library spectrum; S-type of compound determined by direct interpretation of spectrum and retention information.
[3]Quantity per gram of dried plant material estimated by quantitative GC/FID on a DE-1 column with 1.33 mg decane as an internal standard in each sample.
[4]Percentages are approximate, and based on total chemical composition.
[5]Undet. stands for undetermined structure of identified compound.
All extract compositions tested above have insecticidal properties.

Example 10: Refined processing of natural materials to produce a fumigant.

The fumigant properties of *Artemesia tridentata* vasseyana can be concentrated by a modified process of Example 1 set forth above.

Materials and Methods: Harvest and Preparation of Plant Material. *Artemesia tridentata* vasseyana used for the experiment was harvested. Leaves on branches were spread for drying in a 70° F. room. Drying was complete after seven days. Upon drying the leaves easily dropped from the stems of the plants. These were placed in glass jars, flushed with N₂ (Nitrogen) gas, sealed tightly with a Kerr mason jar metal lid, and frozen at 0° F. until the experiment.

New Extract Preparation Process—Leaves were processed according to Example 1 for 2.0 minutes for the control. For the modified process, Super Critical $CO_2$ extraction was used. The initial pressure was 10,000 psi and 40° C. Extracts were stored under nitrogen. The collection flask was partially submerged in an ice bath to prevent carryover into the second flask.

Bioassay with insects—Fumigation chambers used were glass with a teflon lined plastic screw top. Each chamber had an inner capacity of 42 ml. An ethanol (100% absolute) dilution of the equivalent residue of 1 gram of the processed material was added immediately by automatic micropipette to the filter paper folded and placed in the bottom of each test vial. Insects used were unsexed, lesser grain borer adults, *Rhyzopertha dominica* F., 6 to 54 hours after adult emergence. Insects were added to a glass vial (43mm height by 11mm inner diameter). A net cover was placed on the top of the inner vial with a rubber band for gas exchange within the chamber, but still containing the insects. For the control vial, the set up was the same, but minus the treatment with extracted plant material. Control filter paper was treated with an equal volume of absolute ethanol. There was 1 replicate of the control, and 3 replicates of the test material chambers. All chambers were placed in a controlled environment room at 27°±1° C. and 65°±5% relative humidity for the duration of the experiment.

Figure 15:
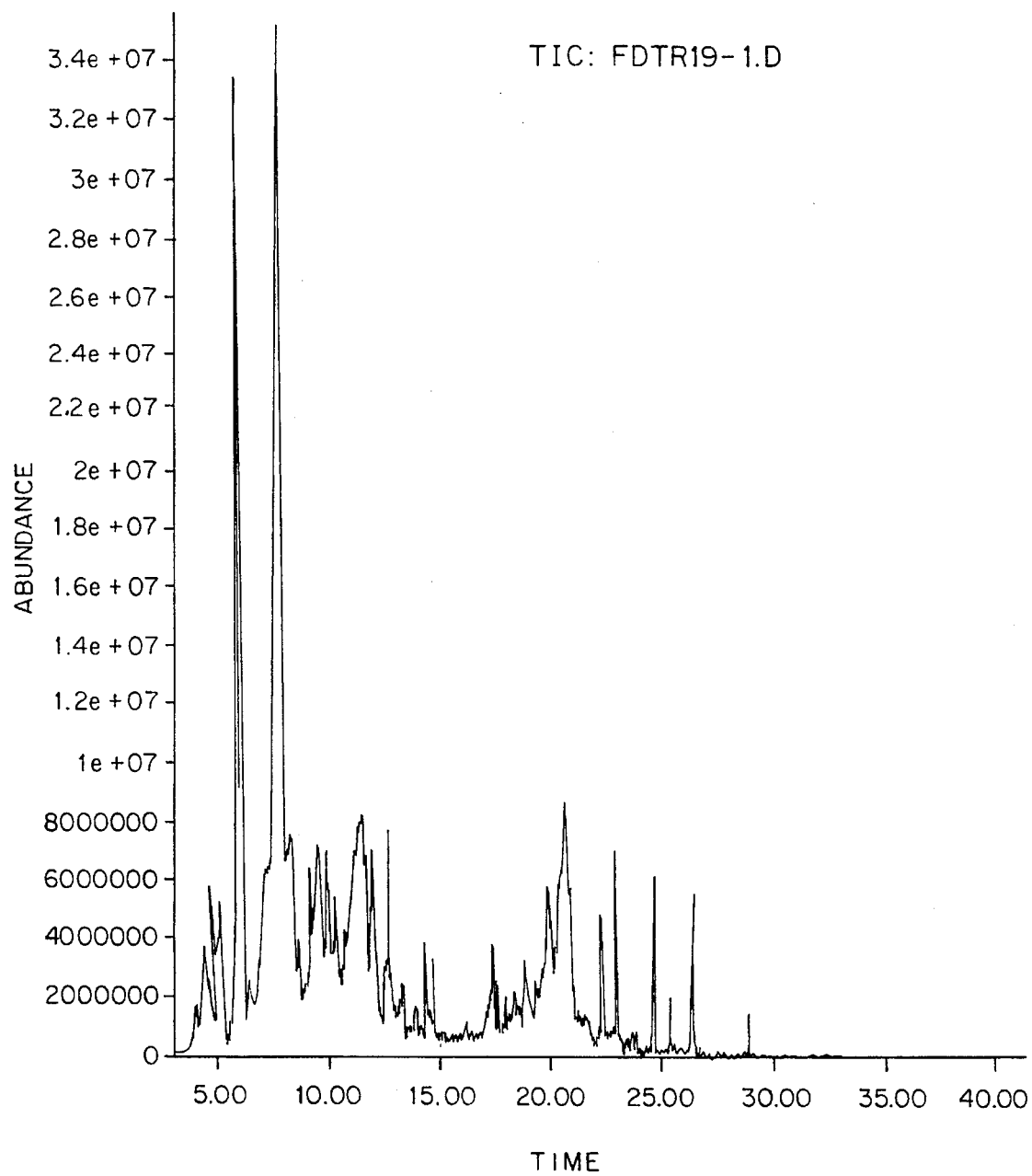
FIGS. 15 and 16 show a gas chromatograph of *Artemesia tridentata* processed according to the concentration procedure of Example 10 herein.
Figure 16:
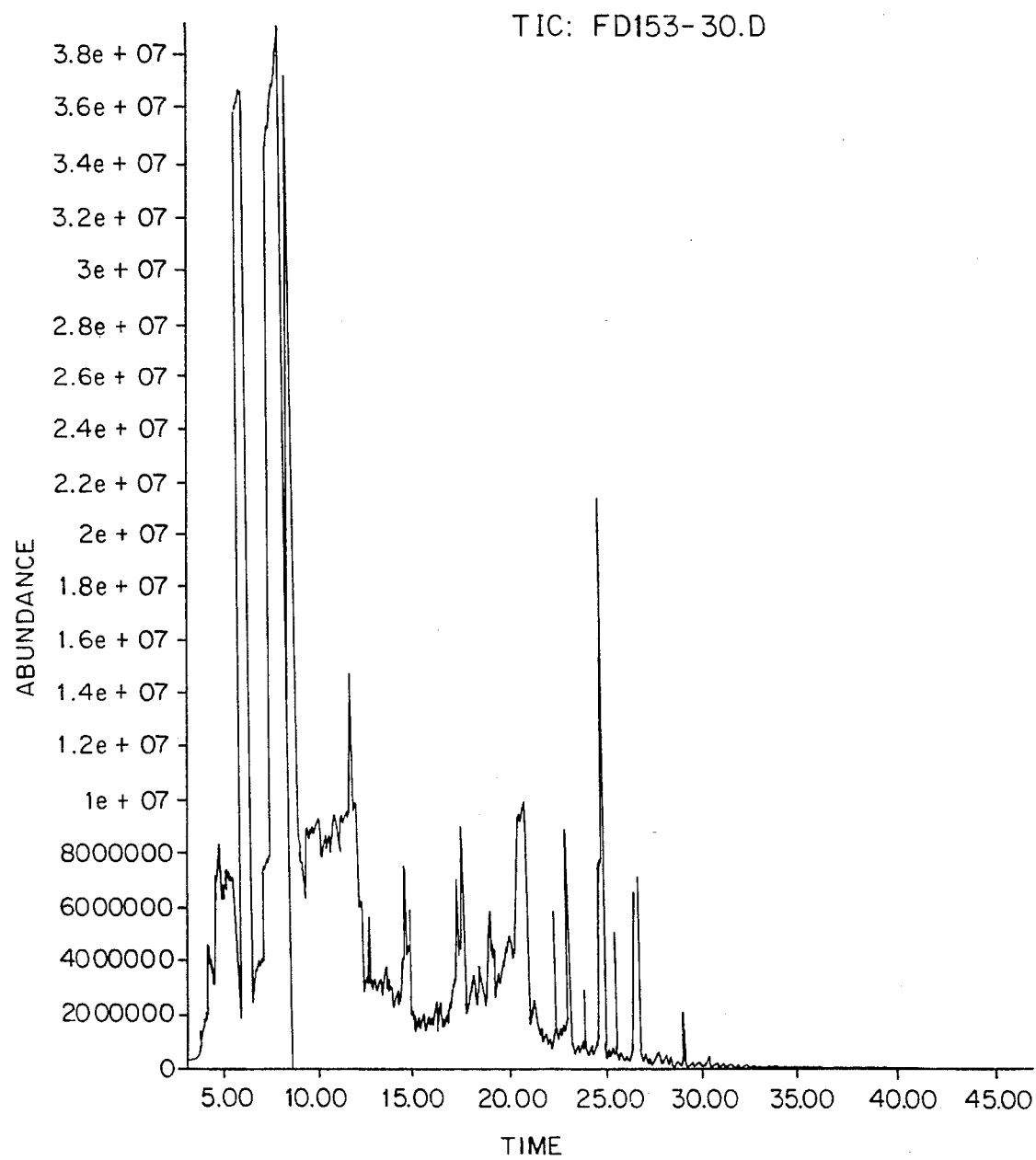

Results: The initial extracts were somewhat resinous, but readily extractable. Analysis of the two extracts were compared with a gas chromatograph. These appear as FIGS. 15 and 16. There are not any apparent differences in the presence/absence of certain peaks.

After a 24 hour fumigation, 70% mortality-/moribundity occurred with leaf material from *A. tridentata* that had been SC-$CO_2$ processed. There seemed to be no difference between insect response to SC-$CO_2$ samples that had been also processed according to Example 1, except with respect to the ratio of mortality to moribundity. Processing according to the Example 1 procedure, plus the $CO_2$ extraction procedure, concentrates the material, making it more convenient to use and retains most of the rapidity of the response.

With the conventional Example 1 procedure, there was an 88% mortality/moribundity within 24 hours.

Conclusions: Super Critical Carbon Dioxide ($CO_2$) extraction can be combined with the process described in Example 1. This combination retains the original per weight action of the processed plant material, but markedly concentrates it. The addition of the second process will provide a product that will be more concentrated.

Example 11: Insect rearing—Four species were reared at 27°±1° C. and 65°±5% relative humidity under a photoperiodic regime of 12:12 light:dark. *Z. subfasciatus* and *A. obtectus* were reared on a diet of dried Pinto beans. *R. dominica* and *S. oryzae* were reared upon a diet of 96:2:2 (w/w) soft white wheat:whole wheat flour:brewers yeast.

Quantification of linalool from *Ocimum canum*—leaves of *Ocimum canum* were collected form the Butare prefecture in Rwanda, air-dried according to traditional practice, and express-shipped to Montana State University where they were stored in a −20° C. freezer prior to bioassay and chemical analysis. The leaves (1.0 g–4 replicates) were milled in a Waring blender for 2 minutes and extracted immediately in 60 ml of 1:4 isopropanol:hexane (containing 40 ng/µl decane as an internal standard) in a 125 ml Erlenmeyer flask for 24 hours. The flasks were covered to prevent photodegradation and occasionally agitated. The resulting solution was directly injected into a gas chromatograph for quantitative analysis. All solvents were purchased from the Sigma Chemical Co., St. Louis, Mo.

Gas chromatography was performed on a Varian model 3700 equipped with a flame-ionization detector containing a 50 m×0.25 mm (i.d.) HP-1 column with a 0.11 µ film thickness; He carrier gas velocity was 31 cm³/s (220° C.). Temperature program-initial temperature 60° C., initial hold 8 min, temperature increase 4° C. per minute, final temperature 260° C.

The linalool peak was tentatively identified using narrow-bore capillary GC-MS. The gas chromatograph was a Varian Model 3700 equipped with a flame ionization detector and a 30.0 m×0.25 mm (i.d.) D85 column with 0.25 µ film thickness: Column conditions used were: He carrier gas velocity—30 cm³/s (220° C.); temperature programming-initial temperature 50° C., initial hold 4.0 min. temperature increase 5.0° C. per minute, final temperature 280° C., final hold 10 min; injector 260° C.; detector temperature 290° C. The electron impact mass spectra were obtained on a VG Analytical model VG 70EHF mass spectrometer operating at 70 eV with a source temperature of 200° C.

Example 12-Leaf exposure bioassay:

Ten adult *Z. subfasciatus*, 5 male and 5 female (0–3 days post-adult eclosion), were added to 5.5 cm glass petri dishes in which 1.0 g of milled, dried leaves of *O. canum* had been distributed evenly throughout the dish. Ten replicates of the treatment and ten replicates of a control (no leaves) were evaluated. Bioassays were evaluated by viewing mortality at 24 and 48 hours, respectively. An insect was considered dead if it was immobile and did not react to probing with a blunt dissecting probe three times. The bioassay conditions were 28°±1° C. at 65±5% R.H. with a photoperiod of 12:12 L:D.

Example 13: Linalool dose-response bioassays.

A 9.0 cm diam. Whatman #1 filter paper was placed in a 10.0 cm diam. glass Corning petri dish. An aliquot of the appropriate dilution of R,S linalool (Sigma Chemical Co., St. Louis, Mo.) was applied to the filter paper in 1.0 ml of absolute ethanol (Quantum Chemical Co., Tuscola, Ill.). The ethanol was evaporated for 20 minutes prior to the addition of the insects. An insect was considered dead if it was immobile and did not react to probing with a blunt dissecting probe three times. Moribundity was assessed by viewing those subsequently righted and viewed carefully. Those that immediately fell onto their backs again as a result of intoxication was classified as moribund. At higher dosages all moribund insects subsequently died. Recovery occurred rarely at low dosages. The bioassy conditions for this and the following bioassay were 27°±2° C. at 65°±8% R.H. with a photoperiod of 12:12 L:D. *Z. subfasciatus* were sexed with 5 males and 5 females used in each replicate; 10 adults of unknown sex were used for the other species.

In a separate experiment, dose-response curves were also prepared for *Z. subfasciatus* using 5 replicates of 10 individuals for each dosage. Counts of mortality and moribundity were terminated after 24 hours.

Bioassay of linalool with increasing duration of air exposure: The protocol was similar to that for the dose-response bioassays. The ethanol in an aliquot delivering 500 µg linalool/cm² to the filter paper was evaporated for 20 minutes and ten replicates of *Z. subfasciatus* (5 male, 5 female; 0–1 days post-adult eclosion) were added immediately. Other replicates were covered immediately after ethanol evaporation and then Zabrotes (as above) were added at times of 0.25 hour, 6 hours, 18 hours and 24 hours post-ethanol evaporation. Mortality/moribundity were determined as above and evaluated at 24 hours after the introduction of the insects into each trial. Ten replicates of an ethanol control were conducted simultaneously for each trial. The bioassay conditions were 28°±1° C. at 65±5% R.H. with a 12:12 light:dark photoperiodic regime.

Quantitative chemical analysis of linalool-treated substrates with increasing duration of air exposure: The air exposure bioassay procedure (above) included four additional replicates. At the time of insect introduction each filter paper for these replicates was handled with forceps, cut into ca. 0.5 cm² pieces and transferred into 125 ml in a Erlenmeyer flask of 1:4 isopropanol: hexane (containing 40 ng/ul decane as an internal standard) in a 250 ml Erlenmeyer flask for 24 hours. The flasks were covered to prevent photodegradation and occasionally agitated. The resulting solution was directly injected into a gas chromatograph for quantitative analysis and GC-MS for identification as per above.

Quantification of linalool from *Ocimum canum*.

Figure 6:
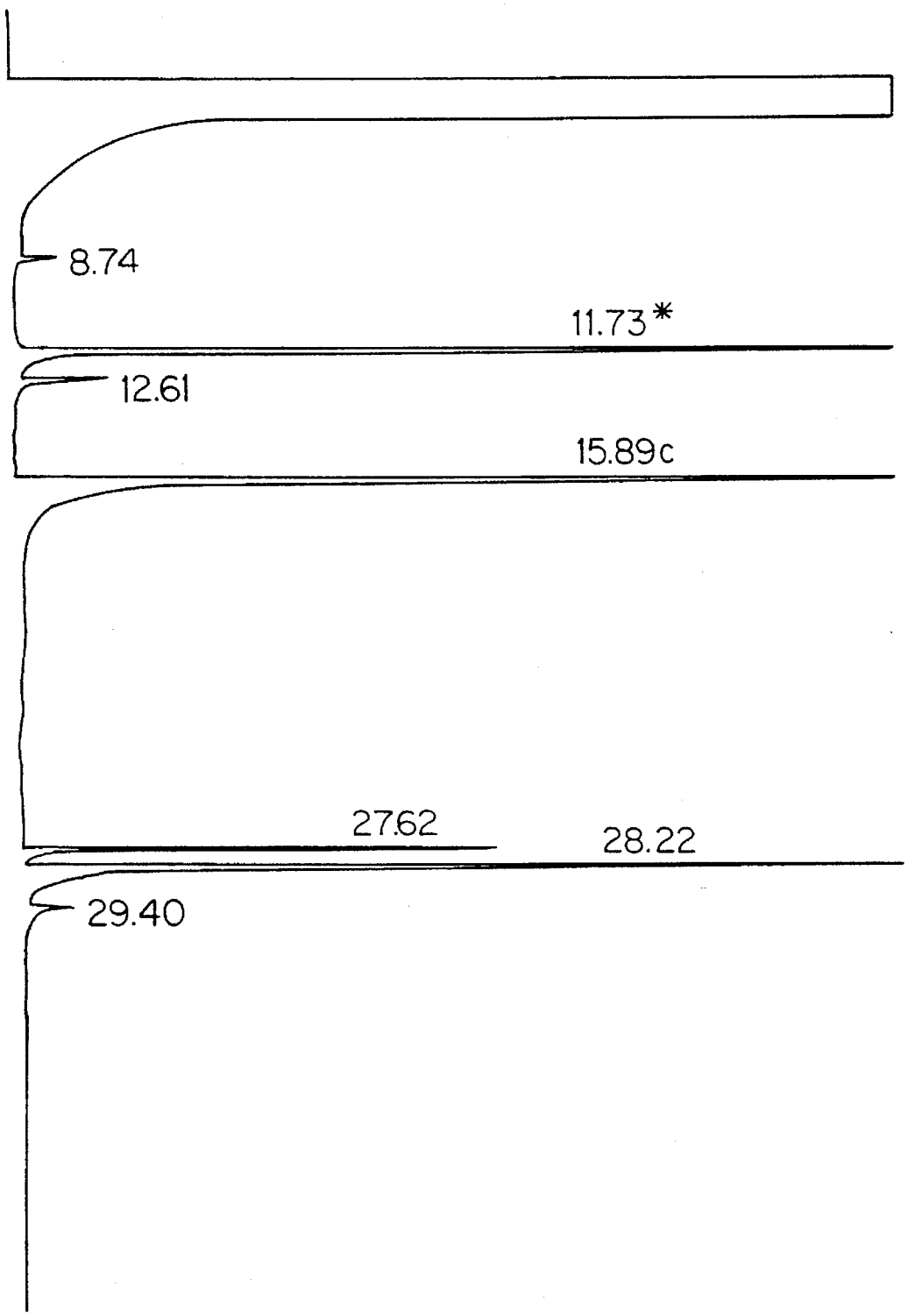
FIG. 6 shows a gas chromatogram of Ig of milled leaves of *Ocimum canum* extracted in 1:4 isopropanol: hexane. Retention times: 11:73-decane (internal standard); 15.89-R, S-linalool.
Figure 7:
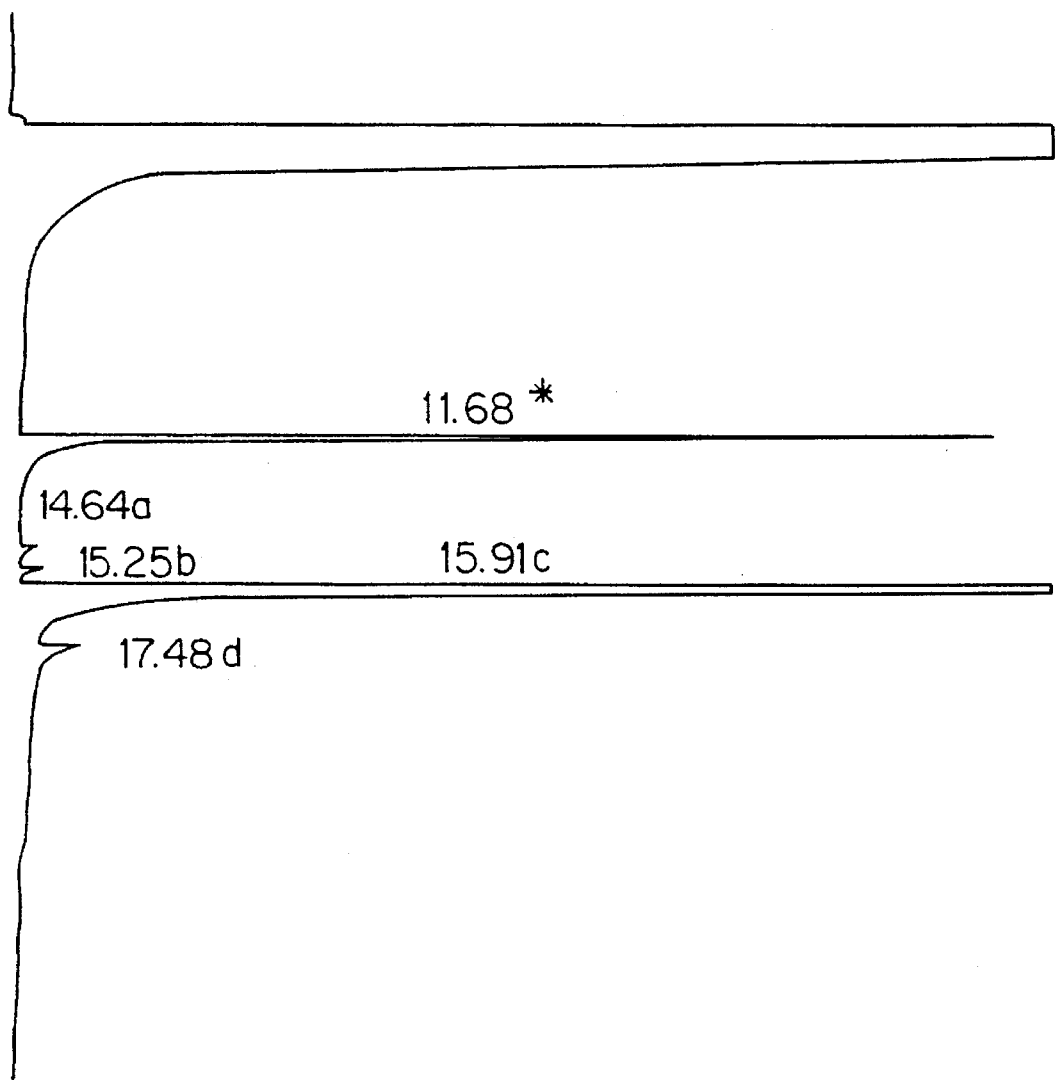
FIG. 7 shows a gas chromatogram of a linalool aliquot (500 µg/cm$^2$) delivered directly into 1:4 isopropanol:hexane. Retention times: 11:68-decane (internal standard); 14.64-beta-myrcene; 15.25-d-limonene; 15.91-R,S-linalool; 17.48-3,7-dimethyl-1-octen-3-ol.

Statistical analysis: The linalool dose-response bioassay data were subject to probit analysis after Abbott's formula was used to adjust for control mortality (Matsumura, 1975). Since the dominant response of the moribund insects was to die, moribundity and mortality were pooled for statistical analysis. Extraction and quantitative gas chromatographic analysis indicated that linalool is present in milled, air-dried leaves of *O. canum* at 8.59±0.92 mg/g. FIG. 6 shows the gas chromatogram of the solvent extract of milled Ocimum leaves; the peak at the retention time of 11.73 is decane (internal standard) and the peak at 15.89 is linalool.

The leaf exposure bioassay indicated 100% mortality of male *Z. subfasciatus* at 24 hours and only 50 mortality of the females at 48 hours. The linalool dose-response bioassays indicated that the $LC_{50}$ values for all four species were similar. The $LC_{50}$ values for each species were: *Z. subfasciatus*-428.3 µg/cm²; *A. obtectus*-412.1 µg/cm²; *R. dominica*-430.2 µg/cm²; *S. oryzae*-426.7 µg/cm² (Table 2). The probit lines for each species are: *Z. subfasciatus*-Y= 13.4408X+−30.3726; *A. obtectus*-Y=11.30808X+−24.7613; *R. dominica*-Y=9.4476X+−19.8818; *S. oryzae*-Y=8.3350X+ −16.9216. Table 3 shows a summary of the mortality data for each dosage.

Increased duration of air exposure of linalool treated substrates had differing effects upon male and female *Z. subfasciatus* susceptibility. The susceptibility of female was halved at fifteen minutes post-ethanol evaporation, whereas the susceptibility of males was not noticeably decreased until eighteen hours post-ethanol evaporation (Table 4).

Dose-responses of male and female *Z. subfasciatus* indicated different $LC_{50}$ values. The $LC_{50}$ value for females was 466.5 µg/cm² with a probit line of Y=8.65X+−18.01: the $LC_{50}$ value for males was 408.5 µg/cm² with a probit line of Y=9.59X+−20.04.

The quantitative analysis indicated that the decrease in susceptibility of female *Z. subfasciatus* at 15 minutes post-solvent evaporation is correlated to a decrease of 50 µg/cm² of linalool at this time. No further increase in the amount of linalool volatilized is evident, nor is any consistent change in the proportions of linalool relative to degradation products evident.

Figure 8:
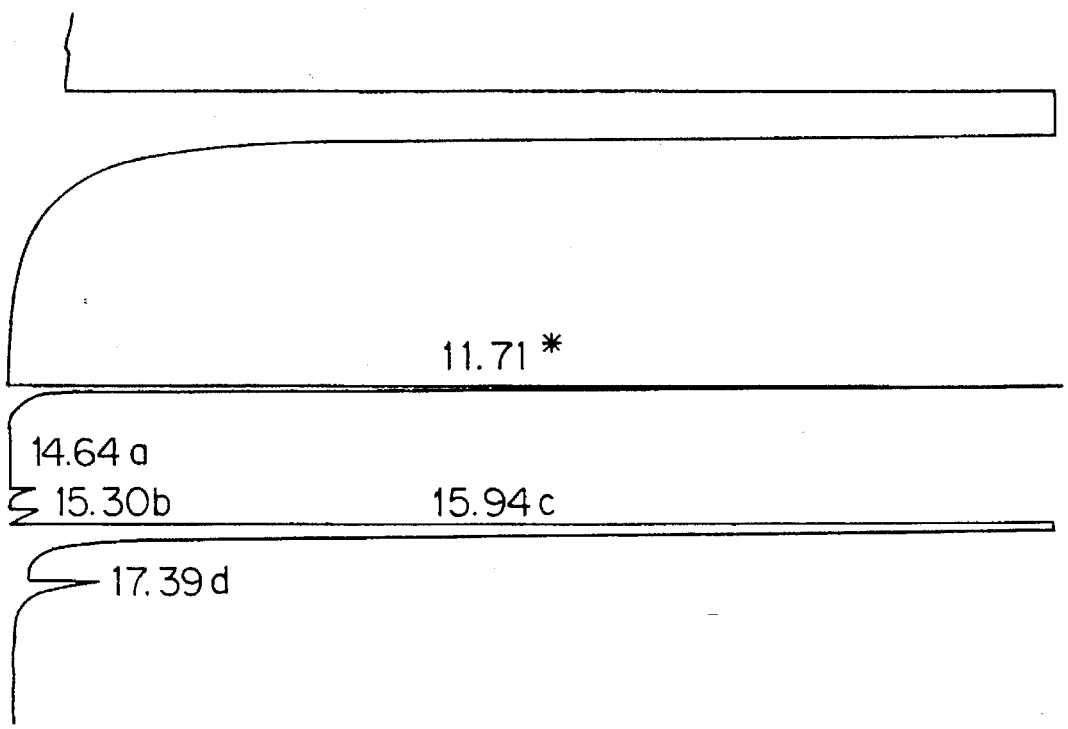
FIG. 8 shows a gas chromatogram of a linalool aliquot applied upon a Whatman #1 filter paper and extracted in 1:4 isopropanol:hexane after 6 hours. Retention times: 11:71-decane (internal standard); 14.64-beta-myrcene; 15.30-d-limonene; 15.94-R,S-linalool; 17.39-3,7-dimethyl-1-octen-3-ol.

The principal degradation products and linalool present in the stock solution (FIG. 6) and after six hours of air-exposure upon Whatman #1 filter paper (FIG. 8) show little variability, qualitatively. The principal peak retention times are: decane-11.7, beta-myrcene-14.6, d-limonene-15.3, R,S-linalool-15.9, and 3,7-dimethyl-1-octen-3-ol 17.4.

TABLE 2

Acute mortality and $LC_{50}$ from fumigation 42 ml vial bioassay of adult stored product insects with freshly milled leaves of big sagebrush, *Artemesia tridentata* (vaseyana) (Compositae). (n = 20;5 insects/rep; 27 ± 2° C.; 65 ± 8% relative humidity; 12:12::light:dark).

| Dose (gram *A. tridentata* milled leaves/cm³ air) | | | | LC50 |
|---|---|---|---|---|
| 0 | 0.0053 | 0.0167 | 0.0294 | (95% confidence interval) |
| *Rhyzopertha dominica* (F.) (0–3 day post adult eclosion; unsexed; 24 hr exposure) | | | | |
| 4 | 32 | 59 | 63 | 0.014 (0.011,0.019) |
| *Rhyzopertha dominica* (F.) (0–3 day post adult eclosion; unsexed; 48 hr exposure) | | | | |
| 10 | 38 | 69 | 85 | 0.010 (0.009,0.012) |
| *Rhyzopertha dominica* (F.) (0–3 day post adult eclosion; unsexed; 72 hr exposure) | | | | |
| 10 | 46 | 72 | 85 | 0.008 (0.006,0.010) |
| *Sitophilus oryzae* (L.) (0–3 day post adult eclosion; unsexed; 72 hr exposure) | | | | |
| 9 | 32 | 62 | 82 | 0.011 (0.010,0.014) |

*Methyl bromide is recommended at 2 lb/1000 ft³ which = 0.321 g/cm³

TABLE 3

Acute mortality and $LT_{50}$ from fumigation 42 ml vial bioassay of adult stored product insects with freshly milled leaves of big mountain sagebrush, *Artemesia tridentata* (vaseyana) (Compositae). (n = 20; 5 insects/rep; 27 ± 2° C.; 65 ± 8% relative humidity; 12:12::light:dark).

| Hours (after inoculation in fumigation chamber) | | | | | | LC50 |
|---|---|---|---|---|---|---|
| 1 | 2 | 6 | 18 | 24 | 48 | 72 | (95% confidence interval) |
| *Rhyzopertha dominica* (F.) (0–3 day post adult eclosion; unsexed; 0.0053 g/cm³ air exposure) | | | | | | |
| 1 | 2 | 6 | 20 | 32 | 38 | 46 | 78.389 (62.451,98.394) |
| *Rhyzopertha dominica* (F.) (0–3 day post adult eclosion; unsexed; 0.0167 g/cm³ air exposure) | | | | | | |
| 1 | 4 | 11 | 45 | 59 | 69 | 72 | 24.100 (20.535,28.284) |
| *Rhyzopertha dominca* (F.) (0–3 day post adult eclosion; unsexed; 0.0294 g/cm³ air exposure) | | | | | | |
| 2 | 3 | 12 | 54 | 63 | 85 | 85 | 17.051 (14.780,19.671) |
| *Sitophilus oryzae* (L.) (0–3 day post adult eclosion; unsexed; 0.0294 g/cm³ air exposure) | | | | | | |
| 0 | 0 | 0 | 2 | 2 | 16 | 82 | 57.137 (52.536,62.141) |

TABLE 4

Oviposition behavior of *Sitophilus oryzae* (L.) exposed to wheat kernels stored with freshly milled leaves of big mountain sagebrush, *Artemesia tridentata* (vaseyana) (Compositae). (5 males and 5 females/rep; 27 ± 2° C.; 65 ± 8% relative humidity; 12:12::light:dark).

*Sitophilus oryzae* (L.) (0–5 day post adult eclosion; 5 females)

| Dose % w/w | # replicates (mean # kernels/rep) | Mean/rep* | | | oviposition location within kernel | | |
|---|---|---|---|---|---|---|---|
| | | OH | P | E + H | germ end | mid-third | distal-third |
| 0 | 8 (32.75) | 106.25 | 95.63 | 63.50 | 38.25 | 43.38 | 21.63 |
| 0.1 | 7 (32.43) | 48.43 | 47.71 | 35.71 | 20.00 | 25.29 | 4.57 |
| 0.2 | 6 (34.83) | 56.67 | 49.50 | 44.67 | 25.83 | 27.17 | 4.83 |
| 0.3 | 7 (32.00) | 57.71 | 52.14 | 46.14 | 22.71 | 25.43 | 8.00 |
| 1.0 | 7 (35.86) | 55.71 | 49.00 | 41.43 | 21.14 | 26.71 | 8.43 |
| 3.0 | 6 (37.00) | 54.83 | 49.83 | 36.50 | 18.67 | 30.5 | 6.17 |

Figure 14A:
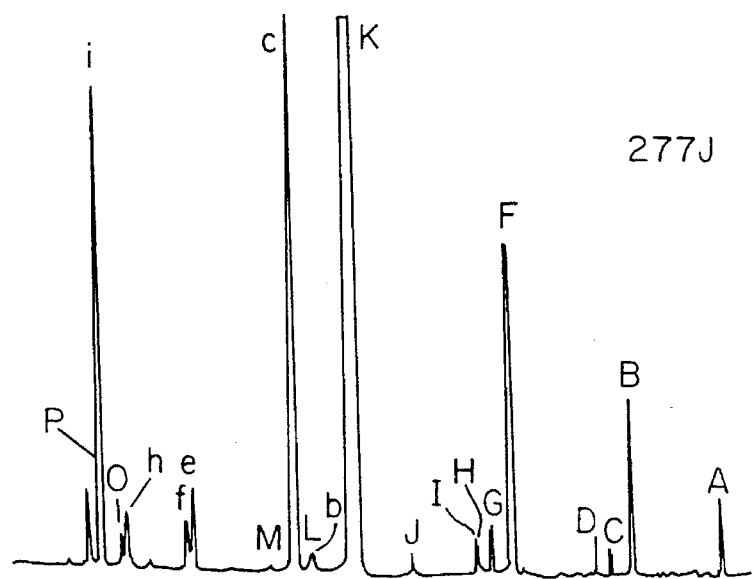
FIG. 14a shows a gas chromatographic scan of the components in *Ocimum canum* sinus leaves after drying and milling.
Figure 14B:
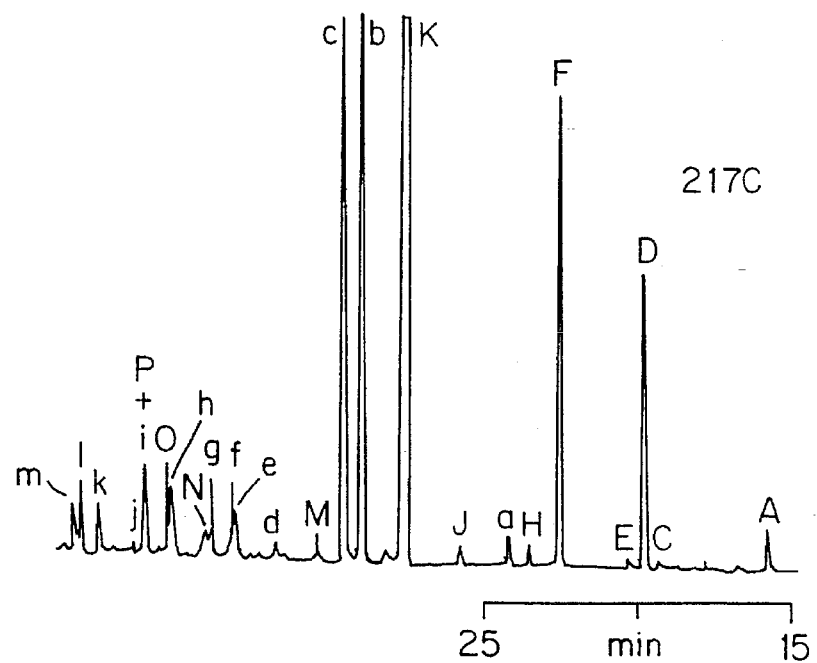
FIG. 14b shows a mass spectrograph of *O. Canum* plants 217C and 277j.

*OH = oviposition holes; E + H = eggs hatched; P = mucilagenous oviposition plug Example 14: FIG. 14 shows a chromatographic scan of the components in *Ocimum canum* sinus leaves two months after drying and milling. *Ocimum canum* hexane extract. Silica gel fractions. 60 degrees (0.5)----->250(5). Internal standard=5 ethyl-2 heptanol (retention time=5.17). Injection prior to run indicated linalool retention time=5.85. This varied from 5.84 to 5.86 due to computer system in the gas chromatograph. Numbers on the scans correspond to the milliliter in which those compounds exited e.g. #5–8 means that fraction came off in the fifth to eighth milliliter from the sample that passed through the column.

Gas chromatography analysis of *Ocimum canum* sinus: Preparative column chromatography A clean (RBS washed) 24.0×0.6 cm (ID) glass column equipped with a Teflon stopcock and a glass wool plug was slurry-packed (1:1 hexane/diethyl ether; HPLC grade) with silica gel (70–230 mesh). Ten ml of the filtered hexane extract of *O. canum* sinus (from the preparation described above) was concentrated under a stream of purified N2 to ca. 500 ul. The concentrated hexane extract was then eluted through the above silica gel column with 1:1 hexane/diethyl ether at a flow rate of 1.0 ml per min. Sixteen labeled 4.0 ml fractions were collected in clean (RBS) vials and sealed with Teflon lined caps. The above fractions were stored at 5° C. to await further use. Capillary gas-liquid chromatography The instrument used was a HP-5890A equipped with flame ionization detector (FID) and a 25.0 m×0.25 mm (ID) fused silica RSL-300 (=OV-17) capillary column. Column conditions used were a carrier gas flow of (Helium) 1.2 cc per min. Temperature program=60° C. (held 0.5 min) raised to 250° C. (held 5.0 min) at 10° C. per min. Injector temperature was 240° C., and detector temperature was 255° C. Injections were 0.5 ml of each (16) of the above preparative fractions co-injected with 0.5 ml of an internal standard (5-ethyl-2-heptanol; retention time (RT)=5.18 min).

Results: The target terpene, linalool (RT=5.81 min determined by injection of a standard), first appeared in fraction #9–12 and was then detected in every fraction through #37–40. Apparently linalool was present in the *O. canum* leaves in great quantity. This accounts for its "tailing" through fractions #37–40. In fact, it is present in fractions #13–16, #17–20, and #21–24 in milligram quantities, with the most occurring in #17–20 (ca. 7.43 mg or 1.86 ug per ul).

Linalool occurs with a number of small "companion" peaks within 0.5 min of its 5.81 min RT; they could be related terpene compounds. Most of these fractions also have several sharply defined peaks between hydrocarbons with 10–20 carbon atoms (alkanes, alkenes, and dienenes). The final calculation from this procedure indicated there was 15 mg linalool in the extract of the 44g of milled leaves or 0.341 mg linalool per g leaves. Although linalool seems to be highly concentrated in the leaves even two months after drying and milling, bioassay procedures with both extract and milled leaves, two months after milling, indicate this may be too low a percent a.i. (active ingredient) to be effective. It is possible that there are the compounds present in much smaller concentrations that enhance the activity of linalool and these synergistic compounds do disappear during the two months following milling.

Table 5 shows a list of extract components from *Ocimum canum*.

TABLE 5

| | Peak | Component | 217C | 277J |
|---|---|---|---|---|
| | — | α-Pinene | 0.3 | 0.2 |
| | | Camphene | 0.1 | 0.1 |
| | | β-Pinene | 0.2 | 0.1 |
| | | Sabinene | 0.1 | t |
| | | Myrcene | 0.2 | 0.4 |
| | | α-Terpinene | 0.1 | t |
| | | Linonene | 0.6 | 0.5 |
| | | 1,β-Cineola | 2.0 | 0.1 |
| | | trans-Hex-2-enal | 0.1 | t |
| | | cis-β-Ocimene | 0.3 | 0.3 |
| | | τ-Terpinene | 0.4 | t |
| | | trans.β-Ocinene | 0.1 | 0.1 |
| | | 3-Octanone | 0.1 | t |
| | | p-Cymene | 0.2 | t |
| | | Terpinolene | t | 0.1 |
| | A | Hexenyl acetate | 0.2 | 0.2 |
| | B | Oct-en-3-yl acetate | — | 0.4 |
| | C | cis-Hex-3-en-1-ol | t | 0.1 |
| | D | 3-Octanol | 1.5 | 0.1 |
| | E | Myrcene epoxide + Fenchone | 0.1 | — |
| | F | Oct-1-en-3-ol | 2.4 | 0.8 |

TABLE 5-continued

| Peak | Component | 217C | 277J |
|---|---|---|---|
| G | Unknown | — | 0.2 |
| H | trans-Sabinene hydrate | 0.1 | t |
| I | Unknown | — | 0.1 |
| a | α-Copaene | 0.2 | — |
| J | Unknown | 0.1 | 0.1 |
| K | cis-Sabinene hydrate | 0.1 | t |
|  | Linalool | 61.0 | 81.1 |
| b | αBergamotene (cis or trans) | 8.2 | t |
| L | Unknown | — | 0.1 |
| c | β-Caryophyllene | 5.3 | 2.8 |
| M | Terpinen-4-ol | 0.2 | t |
| d | Unknown | 0.1 | — |
| e | Unknown | 0.3 | 0.2 |
| f | α-Humulene | 0.5 | 0.2 |
| g | Unknown | 0.5 | — |
| N | δ-Terpineol | 0.1 | — |
| h | Germacrene-D | 0.5 | 0.2 |
| O | α-Terpineol | 0.5 | 0.1 |
| P + 1 | Unknown | 0.8 | 1.3 |
| j | γ-elemene (?) | t | 0.1 |
| k | δ-Cadinene | 0.4 | — |
| l | Unknown | 0.5 | — |
| m | Unknown | 0.3 | — |
|  |  | 83.9 |  | t = trace (<0.05%);(?) - tentatively identified

Example 15: Preliminary bioassay of linalool with *Zabrotes subfasciatu*.

Because the most abundant single chemical component of the hexane extract of milled *O. canum* leaves was linalool, pure (neat) linalool was assayed in 4 concentrations (100 ul, 10 ul, 1.0 ul, and 0.1 ul/ml hexane). 5 male and 5 female *Z. subfasciatus* were placed in each test chamber (9 cm diameter glass petri dish). Solution was allowed to dry. Insects were then added and covered with the upper petri dish. Four hours later (28° C. and continuous light) all insects were dead or moribund at the two highest concentrations.

It was concluded that a definitive linalool bioassay should be done with both *Z. subfasciatus* and *A. obtectus*.

Example 16: Scanning electron microscopy of plant-insect interaction

A Hitachi S570 was used for these studies. Photos were taken with Polaroid film. Specimens were gold coated for 75 seconds (first set of specimens) and 90 seconds (second set of specimens) to a thickness of 200 to 300 angstroms with a sputter coater. The following specimens were examined:

*Z. subfasciatus* (dorsal, ventral, lateral views) exposed to freshly milled *O. canum* leaves

*A. obtectus* (dorsal, ventral, lateral views) exposed to freshly milled *O. canum* leaves

*O. canum* sinus residue from ethanol extraction

*O. canum* sinus residue from hexane extraction

*O. canum* sinus freshly milled leaves.

Example 17: Corrosion Studies: *Artemesia tridentata* vasseyana processed according to Example 1 does not cause corrosion in metals typically present during quarantine, processing plant (such as a flour mill), storage structure, or household fumigations.

Fumigation chambers used were glass with a teflon lined plastic screw top. Each chamber had an inner capacity of 42 ml. *Artemesia tridentata* vasseyana used for the experiment was harvested. Leaves on branches were spread for drying in a 70° room. Drying was completed within seven days. Upon drying, the leaves easily dropped from the stems of the plant. These were placed in glass jars, flushed with $N_2$ (nitrogen) gas, sealed tightly with a Kerr mason jar metal lid, and frozen at 0° until the experiment.

The metals selected were: cold rolled steel, aluminum foil, plated steel, copper (from pipe), brass, stainless steel. With the exception of the aluminum, these metals were polished on a metal lathe until each shone without a smudge. Each piece of metal was 18×7 mm, except for the cold rolled steel which was a cylinder 11 mm in diameter and 10 mm in height.

Leaves were processed by milling in accordance with the present invention for 2.0 minutes. 1 gram of the processed material was added immediately to the bottom of each test vial. A glass vial (43 mm in height by 11 mm inner diameter) was placed open end down on the material. The metal test piece was on top of the glass vial. For the control vial, the set up was the same, but minus the plant material. There was 1 replicate of the control, and 3 replicates of the test material chambers. All chambers were placed in a controlled environment room at 27±1° C. and 65±5% relative humidity for the duration of the experiment.

Results: After 24 hours there was no evidence of a change in the surface condition of any of the metals. After 48 hours there was no change in any of the surface condition of the metals with the exception of the copper. Small 1 $mm^2$ areas (1–2 spots) on each of the treatment replicates appeared, but there was no change in the control. There was no change at 72 hours. There was no further change after 120 hours in any of the metals except the brass, which showed very faint discolorations in areas 2 $mm^2$ in each of the replicates but not in the control.

For a 24 hour fumigation, which is when the insect action, primarily occurs with *A. tridentata*, there is no corrosion problem. With a 48 hour fumigation, there is some caution with copper. No fumigations will extended beyond 72 hours. For the time period of the suggested fumigant action, there is no corrosion problem.

Example 18: A method of rapid screening of aromatic plants which are useful in the present method can be performed using scanning electron microscopy and the glandular hairs of the leaf surface. See FIG. 9.

Thus the invention provides an insecticidal composition comprising a member selected from the group consisting of extracts of leaves of aromatic plants selected from the group consisting of the mint family, the sagebrush family Artemesia (see Tables 2 and 3), including for example: *Artemesia abrotanum, Artemesia absinthium, Artemesia alba, Artemesia annua, Artemesia argyi, Artemesia artica, Artemesia biennis, Artemesia californica, Artemesia campestris, Artemesia campestris pacifica, Artemesia capillaris, Artemesia cana, Artemesia candicans, Artemesia caudata, Artemesia cina, Artemesia discolor, Artemesia douglasiana, Artemesia dracunculus, Artemesia dracunculoides, Artemesia elatior, Aretemesia fasciculata, Artemesia frigida, Artemesia glauca, Artemesia gnaphalodes, Artemesia heterophylla, Artemesia incompta, Artemesia japonica, Artemesia lindleyana, Artemesia litoralis, Artemesia longifolia, Artemesia ludoviciana, Artemesia maritima, Artemesia michauxiana, Artemisia monosperma, Artemesia norvegica, Artemesia nova, Artemesia pacifica, Artemesia papposa, Artemesia pedatifida, Artemesia prescatiana, Artemesia purshii, Artemesia rigida, Artemesia ripicola, Artemesia roxburghiana, Artemesia saxatilis, Artemesia scopulorum, Artemesia spinescens, Artemesia suksdorfii, Artemesia three forked, Artemesia tilesii, Artemesia trifurcata, Artemesia tripartata, Artemesia tridentata, and Artemesia vaseyana, Artemesia vulgaris, Artemesia vulgaris discoloris*, as well as mixtures thereof. Leaves from other aromatic plants include *Geranium viscosissimum, Balsamorhiza sagittata, Ocimum canum*, vapors thereof, and mixtures thereof.

TABLE 6

Artemisia species in the United States and Europe

| | | |
|---|---|---|
| A. araratica | A. haussknectii | A. pontica |
| A. abrotanum | a. herba-alba | A. pycnocephala |
| A. absinthium | A. holoeuca | A. pygmaca |
| A. afghanica | | |
| a. alba | A. incana | A. reptans |
| A. alpina | A. insipida | A. rigida |
| A. annua | A. japonica | A. Rothrockji |
| A. arborescens | A. kurramensis | A. Roxburghiana |
| A. arbuscula | | A. rupestris |
| A. armeniaca | A. laciniata | |
| A. armeniaca | A. lamprocaulos | A. sacranum |
| A. atrata | A. latifolia | A. salsodiodes |
| A. aucheri | a. Lehmaniana | A. santalinifolia |
| A. austriaca | A. lerchiana | A. santanicum |
| | A. lessingians | A. santanicum |
| A. bargusinensis | A. lindleyana | A. scoparia |
| A. barrelieri | A. lobulifolia | A. scopulorum |
| A. biennis | A. longifelia | A. seriota |
| A. bigalovil | A. ludoviciana | A. sivensiana |
| | | A. Skorniakowi |
| A. caerulescens | A. marrantha | A. spicigera |
| A. californica | A. macrocephala | A. spinescens |
| A. campesiris | A. muritima | A. splendens |
| A. carnubi | A. marschalliana | A. stellerana |
| A. caucasica | A. michauxiana | A. stenocephala |
| A. chaineemefolia | A. molineiti | A. suksdorfii |
| A. Cina | A. monogyna | |
| A. Codringiorii | A. monosperma | A. taurica |
| A. commutata | | A. taurica |
| | A. nitda | A. Three-forked |
| A. douglasiana | A. nitrosa | A. tilesli |
| A. dracunculoides | A. navalis | A. tilesli |
| A. dracunculus | A. norvegica | A. tournefortiana |
| A. dzevenowskyi | A. nova | A. trau_vetterana |
| A. eriantra | A. nuriatanica | A. tridentata |
| | A. nutans | A. trifuscata |
| A. filifolin | | A. tripartita |
| A. franscrioides | A. oclandica | A. tschernieviana |
| A. frigida | A. pacifica | A. Turtzaninoviana |
| | A. Palmeri | |
| A. gabrielle | A. paneieii | A. umbelliformis |
| A. genii | A. papposa | A. vallesiaca |
| A. glacialis | A. pauciflora | A. verbotiorum |
| A. glauca | A. pedatfida | A. vulgaris |
| A. gracilescens | A. pedemontana | |
| A. granatensis | A. persica | |

Species of Artemesia.
A. araratica
A. abrotanum
A. Absinthium
A. afghanica
A. alba
A. alba Turra
A. alpina Pallas ex Willd.
A. annua L.
A. arborescens
A. arbuscula
A. armeniaca
A. armeniaca Lam.
A. atrata Lam.
A. Aucheri
A. austriaca Jacq.
A. Austriaca
A. bargusinensis Sprengel
A. barrelieri Besser
A. biennis
A. Bigelovii
A. Biglovii
A. caerulescens
A. californica
A. campestris L.
A. campestris
A. cana
A. carruthii
A. Carruthii
A. caucasica
A. chamaemelifolia Vill.
A. chamaemellifolia
A. Cina
A. Codringtonii
A. commutata Besser
A. douglasiana
A. Douglasiana
A. dracuneuloides
A. dracunculus
A. dracunculus L.
A. Dracunculus
A. dzevanovskyi Leonova
A. eriantha Ten.
A. filifolia
A. franserioides
A. frigida
A. frigida Willd.
A. gabrielle Br.
A. genipi Weber
A. glacialis L.
A. glauca Pallas ex Willd.
A. glauca
A. gracileseens Krasch. & Iljin
A. granatensis Boiss.
A. haussknectii
A. herba-alba
A. herba-alba Asso
A. Herba-alba
A. holocuca Bieb. ex Besser
A. incana
A. insipida Vill.
A. japonica
A. kurramensis
A. laciniata Willd.
A. lamprocaulos
A. latifolia Ledeb.
A. Lehmaniana
A. lerchiana Weber
A. lessingiana Besser
A. lindlevana
A. lobulifolia
A. longifolia
A. ludoviciana
A. macrantha Ledeb.
A. macrocephala
A. maritima
A. maritima group
A. maritima L.
A. marschalliana
A. michauxiana
A. molinieri Quezcl, Barhero, & R. Loisel
A. monogyna
A. monosperma
A. nitda Bertol.
A. nitrosa Weber
A. nivalis Br.-Bl.
A. norvegica
A. norvegica Fries
A. norgegica saxatilis
A. nova
A. nuristanica
A. nutans Willd.

A. oelandica (Besser) Korearoy
A. pacifica
A. Palmeri
A. pancicii (Janka) Ronniger
A. papposa
A. pauciflora Weber
A. pedatifida
A. pedatifida
A. pedemontana Balbis
A. persica
A. pontica L.
A. pycnocephala
A. pygmaca
A. reptans C. Sm. ex Link.
A. rigida
A. Rothrockii
A. Roxburghiana
A. rupestris L.
A. sacrorum
A. Salsoloides Willd.
A. santolinifolia Turcz. ex Krasch.
A. santonicum
A. santonicum L.
A. scoparia Waldst. & Kit.
A. scoparia
A. scopulorum
A. sericca Weber
A. siversiana (Ehrh.) Willd.
A. Skorniakowi
A. spicigera
A. spinscens
A. splendens 7
A. stellerana Besser
A. stenocephala
A. suksdorfil
A. Suksdorfil
A. taurica
A. taurica Willd.
A. Three-forked
A. tilesii
A. tilesii Ledeb.
A. tournefortiana
A. Tournefortiana
A. trautvetterana Besser
A. tridentata
A. trifureata
A. tripartita
A. tschernieviana Besser
A. Turczaninoviana
A. umbeliformis Lam.
A. vallesiaca All.
A. vallesiaca
A. verlotiorum Lamotte
A. vulgaris
A. vulgaris L.

Preferably, the insecticidal composition of the invention comprises one or more extracts of aromatic plants selected from the group consisting of *Geranium viscosissimum*, *Artemesia tridentata*, *Balsamorhiza sagittata*, *O. canum* and *Monarda fistulosa*. In a more preferred embodiment the insecticidal composition comprises one or more extracts of *Geranium viscosissimum* selected from the group consisting of C19 hydrocarbon and Phytol in a range of 0.15 to 0.303 (mg/g), or a range of about 33% to about 67% by weight of the total extract composition.

In an alternative embodiment the composition comprises one or more extracts of *Artemesia tridentata* selected from the group consisting of alpha-Pinene, Camphene, Sabinene, 8-Cineole, Artemisole, cis-p-menth-2-en-1-ol, alpha-Thujone, Myrtenal, Camphor, Pinocarvone, Borneol, cis-Sabinene hydrate, alpha-Terpineol, terpenoid, Isobornyl acetate, Geranyl formate, Ocimenone, trans-Caryophyllene, Germacrene, Nerolidol and sesquiterpene. Preferably the composition comprises each of the extracts of *Artemesia tridentata* set forth above, in a range of 0.047 to 9.708 (mg/g), or between about 0.21% to about 45% by weight of the entire extract composition.

The insecticidal composition may comprise one or more extracts of *Balsamorhiza sagittata* selected from the group consisting of trans-Caryophyllene, Germacrene, Bicyclogermacrene, and Phytol. Preferably the composition comprises each of the extracts of *Balsamorhiza sagittata* set forth above, in a range of 0.405 to 2.179 (mg/g), or between about 11% to about 61% by weight of the entire extract composition. Note synthetic chemicals which duplicate extract components are determined by the invention are intended to be covered by the present invention.

The insecticidal composition alternatively comprises one or more extracts of *Monarda fistulosa* selected from the group consisting of 1-Octen-3-ol, Myrcene, para-Cymene, Limonene, gama-Terpinene, Linalool, Thymoquinone, Thymol, Carvacrol, and Germacrene. Preferably the composition comprises each of the extracts of *Monarda fistulosa* set forth above, in a range of 0.132 to 26.285 (mg/g), or between about 0.36% to about 71% by weight of the entire extract composition. A carrier compound may also be present in the insecticidal composition of the invention. The insecticidal composition alternatively comprises one or more extracts of Ocimum Canum selected from the group consisting of beta-myrcene, d-limonene, R,S-linalool, 3,7 dimentyl 1-octen-3-ol.

Various combinations of chemical extracts of Table 1 may be used in the insecticial compositions of the invention. In addition the insecticidal chemical compositions do not have to be from an extraction process, they can be formulated by a synthetic chemical synthesis process.

The compositions of the invention may be used in a method for the control of insects in an environment by destruction or behavior modification which comprises:

preparing extracts of leaves of one or more aromatic plants, wherein said plants are insecticidal or capable of modifying the behavior of insects, and adding said extracts to said environment in an effective amount such that the insects are controlled by destruction or behavior modification, wherein said plants are aromatic plants selected from the group consisting of the mint family, the sagebrush family Artemesia, *Geranium viscosissimum*, *Balsamorhiza sagittata*, vapors thereof and mixtures thereof.

In the above method the leaves may be finely milled in accordance with Example 1. In an alternative embodiment the above method includes a step of concentrating the extracts by a Super Critical $CO_2$ extraction procedure in accordance with Example 10.

The environment to be treated may include, for example commodity storage areas and closed containers and soil. Insects may be killed by the compositions or the reproduction abilities of the insects may be reduced. Although any insect or mites may be treated with the insecticidal extract compositions of the invention, insects to be treated are preferably are fruit flies, grain borers, grain weevils, dermestids, bostrichids and bean bruchids.

The effective amount of the extract composition is in the range of about 0.1 to about 99 wt.% of the material being protected from the insects.

From the foregoing examples, it will be seen that the invention is broadly applicable for the control and or management of various types of insects using plants as a control material. The plants may be used as bulk material in the form of milled dried leaves or extracts of liquids or vapors may also be used with corresponding results. Additional mixtures of compounds from the extracts and pure or synthetic chemical compounds may be used. It has been discovered unexpectedly, that such materials have an adverse effect on insects particularly in controlled environments such as stored commodity packaging, soil fumigation and the like.

The foregoing descriptions are illustrative of the principles of the invention, the key emphasis being the size of the milled particles. Numerous variations and modifications thereof would be apparent to the person skilled in the art. All such variations and modifications are to be considered to be in the spirit and scope of the invention.

I claim:

1. An insecticidal composition capable of killing insects, comprising an insecticidal amount of a composition made by a process of preparing a solid super critical $CO_2$ extract of dried leaves of mixtures of two or more aromatic plants selected from the group consisting of the mint family, the sagebrush genus Artemisia, *Geranium viscosissimum,* and *Balsamorhiza sagittata*; and vapors of said composition.

2. A composition according to claim 1 wherein said dried leaves are finely milled to an average particle size of 2 mm$^2$ or smaller.

3. A composition according to claim 1, wherein said composition further comprises a carrier.

4. A composition according to claim 3, wherein said carrier is selected from the group consisting of ethanol, hexane and isopropyl alcohol.

5. A composition according to claim 1, wherein said aromatic plant is selected from the group consisting of *Ocimum canum, Artemisia tridentata, Balsamorhiza sagittata* and *Monarda fistulosa.*

6. The composition according to claim 1, wherein said aromatic plant of the sagebrush genus Artemisia is selected from the group consisting of *Artemisia abrotanum, Artemisia absinthium, Artemisia alba, Artemisia annua, Artemisia argyi, Artemisia artica, Artemisia biennis, Artemisia californica, Artemisia campestris, Artemisia campestris pacifica, Artemisia capillaris, Artemisia cana, Artemisia candicans, Artemisia caudata, Artemisia cina, Artemisia discolor, Artemisia douglasiana, Artemisia dracunculus, Artemisia dracunculoides, Artemisia elatior, Artemisia fasciculata, Artemisia frigida, Artemisia glauca, Artemisia gnaphalodes, Artemisia heterophylla, Artemisia incompta, Artemisia japonica, Artemisia lindleyana, Artemisia litoralis, Artemisia longifolia, Artemisia ludoviciana, Artemisia maritima, Artemisia michauxiana, Artemisia monosperma, Artemisia norvegica, Artemisia nova, Artemisia pacifica, Artemisia papposa, Artemisia pedatifida, Artemisia prescatiana, Artemisia purshii, Artemisia rigida, Artemisia ripicola, Artemisia roxburghiana, Artemisia saxatilis, Artemisia scopulorum, Artemisia spinescens, Artemisia suksdorfii, Artemisia three forked, Artemisia tilesii, Artemisia trifurcata, Artemisia tripartata, Artemisia tridentata,* and *Artemisia vaseyana, Artemisia vulgaris, Artemisia vulgaris discoloris,* and mixtures thereof.

7. The composition according to claim 1, wherein said super critical $CO_2$ extract comprises two or more compounds selected from the group consisting of C19 hydrocarbon and Phytol.

8. The composition according to claim 1, wherein said super critical $CO_2$ extract comprises two or more compounds selected from the group consisting of alpha-Pinene, Camphene, Sabinene, 8-Cineole, Artemisole, cis-p-menth-2-en-1-ol, alpha-Thujone, Myrtenal, Camphor, Pinocarvone, Borneol, cis-Sabinene hydrate, alpha-Terpineol, terpenoid, Isobornyl acetate, Geranyl formate, Ocimenone, trans-Caryophyllene, Germacrene, Nerolidol and sesquiterpene.

9. The composition according to claim 1, wherein said super critical $CO_2$ extract comprises two or more compounds selected from the group consisting of trans-Caryophyllene, Germacrene, Bicyclogermacrene and Phytol.

10. The composition according to claim 1, wherein said super critical $CO_2$ extract comprises two or more compounds selected from the group consisting of 1-Octen-3-ol, Myrcene, para-Cymene, Limonene, gama-Terpinene, Linalool, Thymoquinone, Thymol, Carvacrol and Germacrene.

11. The composition according to claim 1, wherein said super critical $CO_2$ extract comprises two or more compounds selected from the group consisting of beta-myrcene, d-limonene, R,S-linalool and 3,7 dimethyl 1-octen-3-ol.

12. An insecticidal composition comprising an insecticidal amount of a composition comprising mixtures of compounds selected from the group consisting of alpha-Pinene, Camphene, Sabinene, 8Cineole, Artemisole, cis-p-menth-2-en-1-ol, alpha-Thujone, Myrtenal, Camphor, Pinocarvone, Borneol, cis-Sabinene hydrate, alpha-Terpineol, terpenoid, Isobornyl acetate, Geranyl formate, Ocimenone, trans-Caryophyllene, Germacrene, Nerolidol and sesquiterpene.

13. A composition capable modifying the behavior of insects, comprising an insect behaviorally active amount of a composition made by a process of preparing a solid super critical $CO_2$ extract of dried leaves of mixtures of two or more aromatic plants selected from the group consisting of the mint family, the sagebrush genus Artemisia, *Geranium viscosissimum* and *Balsamorhiza sagittata;* and vapors of said composition.

14. A composition according to claim 13, wherein said composition is an insect repellant.

15. A method for the control of insects in an environment by destruction or behavior modification which comprises:

preparing a solid super critical $CO_2$ extract of dried leaves of mixtures of two or more aromatic plants selected from the group consisting of the mint family, the sagebrush genus Artemisia, *Geranium viscosissimum* and *Balsamorhiza sagittata;* and adding said extract to said environment in an effective amount such that the insects are controlled by destruction or behavior modification.

16. The method according to claim 15, wherein said super critical $CO_2$ extract comprises two or more compounds selected from the group consisting of alpha-Pinene, Camphene, Sabinene, 8-Cineole, Artemisole, cis-p-menth-2-en-1-ol, alpha-Thujone, Myrtenal, Camphor, Pinocarvone, Borncol, cis-Sabinene hydrate, alpha-Terpineol, terpenoid, Isobornyl acetate, Geranyl formate, Ocimenone, trans- Caryophyllene, Germacrene, Nerolidol, sesquiterpene, Phytol, limonene, linalool, thymol, myrcrene and di-methyl-1-octen-3-ol.

17. The method according to claim 15, wherein said environment comprises commodity storage areas and closed containers and said control of insects is by reduction in population.

18. The method according to claim 15, wherein said environment comprises soil.

19. A method according to claim 15, wherein the leaves are milled to an average particle size of 1.0 mm$^2$ or smaller.

20. A method according to claim 15, wherein the insects are fruit flies, stored grain insects, bean bruchids, bostrichids and dermestids.

21. A method according to claim 15, wherein the effective amount is 0.1 to 99 wt. % of the material being protected from the insects.

22. The method according to claim 15, wherein said extract is derived from glandular hairs or trichomes on an intact leaf which is a storage unit for components of the insecticidal composition.

23. A method for the control of insects by reductions in population in commodity storage areas and closed containers which comprises contacting the insects with the insecticidal composition of claim 1.

24. A method for fumigation of soil which comprises contacting the soil with an insecticidal composition of claim 1.

* * * * *